(12) United States Patent
Aran et al.

(10) Patent No.: US 11,905,552 B2
(45) Date of Patent: Feb. 20, 2024

(54) IMMOBILIZED RNPS FOR SEQUENCE-SPECIFIC NUCLEIC ACID CAPTURE AND DIGITAL DETECTION

(71) Applicant: KECK GRADUATE INSTITUTE, Claremont, CA (US)

(72) Inventors: Kiana Aran, Pasadena, CA (US); Tara deBoer, Berkeley, CA (US); Irina Conboy, Berkeley, CA (US)

(73) Assignees: KECK GRADUATE INSTITUTE OF APPLIED LIFE SCIENCES, Claremont, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 685 days.

(21) Appl. No.: 15/998,353

(22) Filed: Aug. 6, 2018

(65) Prior Publication Data
US 2019/0112643 A1    Apr. 18, 2019

Related U.S. Application Data

(60) Provisional application No. 62/597,806, filed on Dec. 12, 2017, provisional application No. 62/541,100, filed on Aug. 4, 2017.

(51) Int. Cl.
| | |
|---|---|
| *C12Q 1/6825* | (2018.01) |
| *C12Q 1/6806* | (2018.01) |
| *C12Q 1/6811* | (2018.01) |
| *C12N 9/22* | (2006.01) |
| *G01N 27/327* | (2006.01) |
| *G01N 27/414* | (2006.01) |

(52) U.S. Cl.
CPC ........... *C12Q 1/6825* (2013.01); *C12N 9/22* (2013.01); *C12Q 1/6806* (2013.01); *C12Q 1/6811* (2013.01); *G01N 27/3272* (2013.01); *G01N 27/4145* (2013.01); *G01N 27/4146* (2013.01)

(58) Field of Classification Search
CPC .. C12Q 1/6825; C12Q 1/6806; C12Q 1/6811; C12N 9/22; G01N 27/3272; G01N 27/4145
See application file for complete search history.

(56) References Cited

U.S. PATENT DOCUMENTS

| | | | |
|---|---|---|---|
| 5,827,482 A | 10/1998 | Shieh et al. | |
| 6,150,106 A | 11/2000 | Martin et al. | |
| 8,815,162 B2 | 8/2014 | Vossenaar et al. | |
| 2004/0238379 A1 | 12/2004 | Lindsay et al. | |
| 2005/0170347 A1 | 8/2005 | Miyahara et al. | |
| 2005/0191683 A1 | 9/2005 | Yoo et al. | |
| 2006/0016699 A1 | 1/2006 | Kamahori et al. | |
| 2006/0141474 A1 | 6/2006 | Miyahara et al. | |
| 2007/0231211 A1 | 10/2007 | Yoo et al. | |
| 2008/0283875 A1 | 11/2008 | Mukasa et al. | |
| 2009/0208922 A1 | 8/2009 | Choi et al. | |
| 2011/0165557 A1 | 7/2011 | Ah et al. | |
| 2011/0217763 A1 | 9/2011 | Rasooly et al. | |
| 2012/0021918 A1 | 1/2012 | Bashir et al. | |
| 2012/0214172 A1 | 8/2012 | Chen et al. | |
| 2013/0056367 A1 | 3/2013 | Martinez et al. | |
| 2013/0089932 A1 | 4/2013 | Wu et al. | |
| 2013/0140518 A1 | 6/2013 | Jain et al. | |
| 2013/0164859 A1 | 6/2013 | Johnson et al. | |
| 2013/0204107 A1 | 8/2013 | Lee et al. | |
| 2013/0307029 A1 | 11/2013 | Xu et al. | |
| 2014/0162390 A1 | 6/2014 | Afzali-Ardakani et al. | |
| 2014/0312879 A1 | 10/2014 | Torsi et al. | |
| 2015/0038378 A1 | 2/2015 | Cheng et al. | |
| 2015/0218094 A1 | 8/2015 | Braunschweig et al. | |
| 2015/0308977 A1 | 10/2015 | Saito et al. | |
| 2016/0265047 A1 | 9/2016 | Van Rooyen et al. | |
| 2017/0350882 A1 | 12/2017 | Lin et al. | |
| 2018/0355380 A1 | 12/2018 | Shuber et al. | |

FOREIGN PATENT DOCUMENTS

| | | |
|---|---|---|
| EP | 1843157 | 10/2007 |
| JP | WO2005090961 | 2/2008 |
| WO | WO2005029059 | 3/2005 |
| WO | WO2008076406 | 6/2008 |
| WO | WO2014176524 | 10/2014 |
| WO | WO2016028843 | 2/2016 |
| WO | WO2016100049 | 6/2016 |
| WO | WO2016145110 | 9/2016 |

OTHER PUBLICATIONS

Lou (Analytical Chemistry (2015) vol. 87, pp. 1145-1151).*
Chylinkski ( Nucleic acids research (2014) vol. 42, pp. 6091-6105).*
Yan(Biosensors and Bioelectronics (2009) vol. 24, pp. 1241-1245).*
Zheng (ACS Applied Materials & interfaces (2015), vol. 7, pp. 16953-16959).*
Zhang (Materials Science and Engineering X (2013) vol. 13, pp. 3851-3857).*
Ronkainen (Chem. Soc. Rev., 2010, 39, 1747-1763).*
Pardee (cell (2016) vol. 165, pp. 1255-1266).*

(Continued)

*Primary Examiner* — Steven Pohnert
(74) *Attorney, Agent, or Firm* — Workman Nydegger; Logan B. Christenson

(57) ABSTRACT

A digital biosensor for assaying a target nucleic acid and methods of using the biosensor for digitally detecting the target nucleic acid are disclosed wherein the biosensor includes a substrate having a substrate surface and at least two electrodes, a linker molecule having a first moiety conjugated to the substrate surface, a ribonucleoprotein (RNP) conjugated to a second moiety of the linker molecule, and a guide ribonucleic acid (gRNA) having a first sequence capable of binding to the inactive RNP and a second sequence capable of binding to the target nucleic acid.

16 Claims, 20 Drawing Sheets

(20 of 20 Drawing Sheet(s) Filed in Color)

Specification includes a Sequence Listing.

(56) References Cited

OTHER PUBLICATIONS

Teker (NanoBiotechnology (2005) pp. 171-182).*
Sethuraman (Potential Applications of Carbon Nanotubes in Bioengineering( Biolelectric Engineering (2004) vol. two, pp. 51-68).*
Katz (ChemPhysChem 2004, 5, 1084-1104).*
Cho et al., "Targeted genome engineering in human cells with the Cas9 RNA-guided endonuclease," Nature Biotechnology, Mar. 2013; 31(3):230-232.
Dang et al., "Optimizing sgRNA structure to improve CRISPR-Cas9 knockout efficiency," Genome Biology, 2015; 16:280; 10 pgs.
Everaerts et al., "Biomechanical properties of carbodiimide crosslinked collagen: Influence of the formation of ester crosslinks," Journal of Biomedical Materials Research Part A, 2007:547-555.
Geogakilas et al., "Functionalization of Graphene: Covalent and Non-Covalent Approaches, Derivatives, and Applications," Chem. Rev., 2012; 112:6156-6214.
Lee et al., "Nanoparticle delivery of Cas9 ribonucleoprotein and donor DNA in vivo induces homology-directed DNA repair," Nat Biomed Eng., Author Manuscript, May 25, 2018; 39 pgs.
Schwierz, Frank, "2D Materials Beyond Graphene For Future Electronics," Apr. 15, 2015, Ilmenau University of Technology; 26 pgs.
Wang et al., "Different EDC/NHS Activation Mechanisms between PAA and PMAA Brushes and the Following Amidation Reactions," Langmuir, 2011; 27:12058-12068.
Afsahi, Savannah J., et al., "Towards Novel Graphene-Enabled Diagnostic Assays with Improved Signal-to-Noise Ratio", MRS Advances, 2017 Materials Research Society.
Afsahi, Savannah, et al., "Novel graphene-based biosensor for early detection of Zika virus infection", Biosensors and Bioelectronics 100 (2018), Accepted Aug. 23, 2017.
Aran, Kiana, Ph.D., "Next Generation Graphene Transistors for Biological Threat", Biosensors for Pandemics 2021.
Balderston, Sarah, et al., "Discrimination of single-point mutations in unamplified genomic DNA via Cas9 immobilized on a graphene field-effect transistor", Nature Biomedical Engineering, vol. 5, Jul. 2021.
Bruch, Richard, et al., "Unamplified gene sensing via Cas9 on graphene", Nature Biomedical Engineering, vol. 3, Jun. 2019.
Cheng, Zengguang, et al., "Suspended Graphene Sensors with Improved Signal and Reduced Noise", Nano Letters, 2010.
Dontschuk, Nikolai, et al., "A graphene field-effect transistor as a molecule-specific probe of DNA nucleobases", Nature Communications, Published Mar. 24, 2015.
Gao, Zhaoli, et al., "Scalable Production of Sensor Arrays Based on High-Mobility Hybrid Graphene Field Effect Transistors", Applied Materials & Interfaces, Published Sep. 27, 2016.
Green, Nathaniel S., et al., "Interactions of DNA with graphene and sensing applications of graphene field-effect transistor devices: a Review", Analytica Chimica Acta, 2015.
Hajian, Reza, et al., "Rapid and Electronic Identification and Quantification of Age-Specific Circulating Exosomes via Biologically Activated Graphene Transistors", Advanced Biology 2021.
Koo, Bonhan, et al., "CRISPR/dCas9-mediated biosensor for detection of tick-borne diseases", Sensors and Actuators B: Chemical, 2018.
Kybert, Nicholas J., et al., "Scalable arrays of chemical vapor sensors based on DNA-decorated graphene", Nano Research 2014, Accepted Oct. 12, 2013.
Palla, Mirko, et al., "Single-Molecule Characterization of a Nanopore-Coupled Cas9 Protein on an Electrode Array", Retrieved 2021.
Pardee, Keith, et al., "Rapid, Low-Cost Detection of Zika Virus Using Programmable Biomolecular Components", 2016, Cell, May 19, 2016.
Sadlowski, Corinne, et al., "Graphene-based biosensor for on-chip detection of Bio-orthogonally Labeled Proteins to Identify the Circulating Biomarkers of Aging during Heterochronic Parabiosis", Lab Chip, Oct. 23, 2018.
Cormac Sheridan, "COVID-19 spurs wave of innovative diagnostics", Nature Biotechnology, vol. 38, Jul. 2020.
Singh, Digvijay, et al., "Mechanisms of improved specificity of engineered Cas9s revealed by single molecule FRET analysis", Nat Struct Mol Biol. Apr. 2018.
Xu, Guangyu, et al., "Electrophoretic and field-effect graphene for all-electrical DNA array technology", Nature Communications, Published Sep. 5, 2014.
Yang, Wayne, et al., "Detection of CRISPR-dCas9 on DNA with Solid-State Nanopores", Nano Letters 2018, Published Sep. 6, 2018.
Zhan, Beibei, et al., "Graphene Field-Effect Transistor and Its Application for Electronic Sensing", Small 2014, 10, No. 20, 4042-4065.
Zuccaro, Laura, et al., "Real-Time Label-Free Direct Electronic Monitoring of Topoisomerase Enzyme Binding Kinetics on Graphene", ACS Nano, vol. 9, No. 11, 11166-11176, 2015.

* cited by examiner

CRISPR-functionalized
graphene field-effect biosensor

Detection time < 5 min

SIGNAL: +

SIGNAL: −

IMMOBILIZED RNPS FOR SEQUENCE-SPECIFIC NUCLEIC ACID CAPTURE AND DIGITAL DETECTION

CROSS-REFERENCE TO RELATED APPLICATION(S)

The present application claims priority to and the benefit of U.S. Provisional Application Ser. No. 62/541,100 entitled "CRISPR-Based Graphene Biosensor For Digital Detection of DNA Mutations," filed on Aug. 4, 2017, and U.S. Provisional Application Ser. No. 62/597,806 entitled "Real Time On-Chip PCR-Free Digital Gene Detection Using CRISPR," filed on Dec. 12, 2017, the entire contents of both of which are incorporated herein by reference.

INCORPORATION BY REFERENCE

The instant application contains a Sequence Listing which has been submitted in ASCII format via EFS-Web and is hereby incorporated by reference in its entirety. Said ASCII copy was created on Dec. 24, 2018, is named 161168SEQ-LISTING.txt, and is 1,188 bytes in size.

BACKGROUND

Point-of-care (POC) molecular diagnostics hold the power to provide physicians with actionable information to improve patient outcomes and introduce precision medicine treatment approaches. Specifically, nucleic acid-based POC tests could be implemented to guide therapy and detect endemic infectious diseases such as tuberculosis, HIV and ZIKA. Most conventional methods for nucleic acid-based molecular diagnostic tests require sample preparation and amplification using polymerase chain reaction (PCR), which requires trained personnel and complex instrumentation to detect the signal. As such, new strategies are needed to overcome the resource limitations associated with current PCR-based molecular diagnostics to afford fully integrated and portable POC nucleic acid-based diagnostics.

SUMMARY

In some embodiments of the present disclosure, a biosensor for assaying a target nucleic acid includes a substrate comprising a substrate surface and at least two electrodes, a linker molecule having a first moiety conjugated to the substrate surface, a ribonucleoprotein (RNP) conjugated to a second moiety of the linker molecule, and a guide ribonucleic acid (gRNA) comprising a first sequence capable of binding to the RNP and a second sequence capable of binding to the target nucleic acid. The RNP may be active or inactive. The RNP may be selected from a type I, a type II, or a type III Cas protein or a Madagascar nuclease protein. The Madagascar nuclease protein may be MAD7. In some embodiments the RNP is an active or inactive Cas9, wherein when the RNP is an active Cas9, the biosensor may also include a divalent cation.

In some embodiments, the substrate surface is selected from silicon, silicon oxide, silicon dioxide (glass), or paper.

In some embodiments of the present disclosure, the substrate may be or have a modified surface where the substrate surface of the biosensor is selected from graphene, silicone, germanene, graphene nanoribbons (GNR), bilayer graphene (BLG), phosphorene, stanine, graphene oxide, reduced graphene, fluorographene, $MoS_2$, gold, or carbon.

In some embodiments, the substrate of the biosensor includes a transistor having a source electrode, a drain electrode, and a gate electrode. In some embodiments, the transistor is a field-effect transistor.

The biosensor of claim 1, wherein the first moiety of the linker molecule is capable of binding to graphene, silicone, germanene, graphene nanoribbons (GNR), bilayer graphene (BLG), phosphorene, stanine, graphene oxide, reduced graphene, fluorographene, $MoS_2$, gold, or carbon.

In some embodiments of the present disclosure, a method of assaying the target nucleic acid in a sample of genomic deoxyribonucleic acid (DNA) includes using the biosensor of the present disclosure, the method including administering the sample to the substrate surface of the biosensor, applying a current to the substrate, and measuring a change in the current upon binding of the target nucleic acid to the gRNA. In some embodiments, the sample is a human biological sample selected from urine, blood, serum, cerebral fluid, or saliva and the target nucleic acid is a DNA sequence in a gene corresponding to a disease.

In some embodiments, a method of assaying a candidate guide ribonucleic acid (gRNA) using the biosensor disclosed herein, the method including administering a composition comprising the target nucleic acid to the biosensor, applying a current to the substrate, and measuring a change in the current, wherein a change in the current occurs upon binding of the target nucleic acid to the candidate gRNA.

In some embodiments, a biosensor for assaying a plurality of different target nucleic acids in a first sample includes a substrate having a plurality of substrate surfaces and at least two electrodes coupled to each of the plurality of substrate surfaces, a plurality of linker molecules each having a first moiety and each of the plurality of linker molecules conjugated to one of the plurality of substrate surfaces, a plurality of inactive ribonucleoproteins (RNPs) each conjugated to the second moiety of one of the plurality of linker molecules, and a plurality of guide ribonucleic acids (gRNAs) each having one of plurality of first sequences capable of binding to one of the plurality of the inactive RNPs and one of a plurality of second sequences capable binding to one of the plurality of different target nucleic acids.

In some embodiments of the present disclosure, a method of assaying a plurality of candidate inactive RNPs and a plurality of candidate gRNPs for capturing a target nucleic acid includes using the biosensor of the present disclosure, the method including administering a composition having the target nucleic acid to the biosensor, applying a current to the substrate, and measuring an electrical property of the current at each of the plurality of substrate surfaces, wherein a change in the electrical property occurs upon binding of the target nucleic acid to one of the candidate gRNAs bound to one of the candidate inactive RNPs.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The accompanying drawings, together with the specification, illustrate example embodiments of the present disclosure, and, together with the description, serve to explain the principles of the present disclosure.

DETAILED DESCRIPTION

Figure 1A:
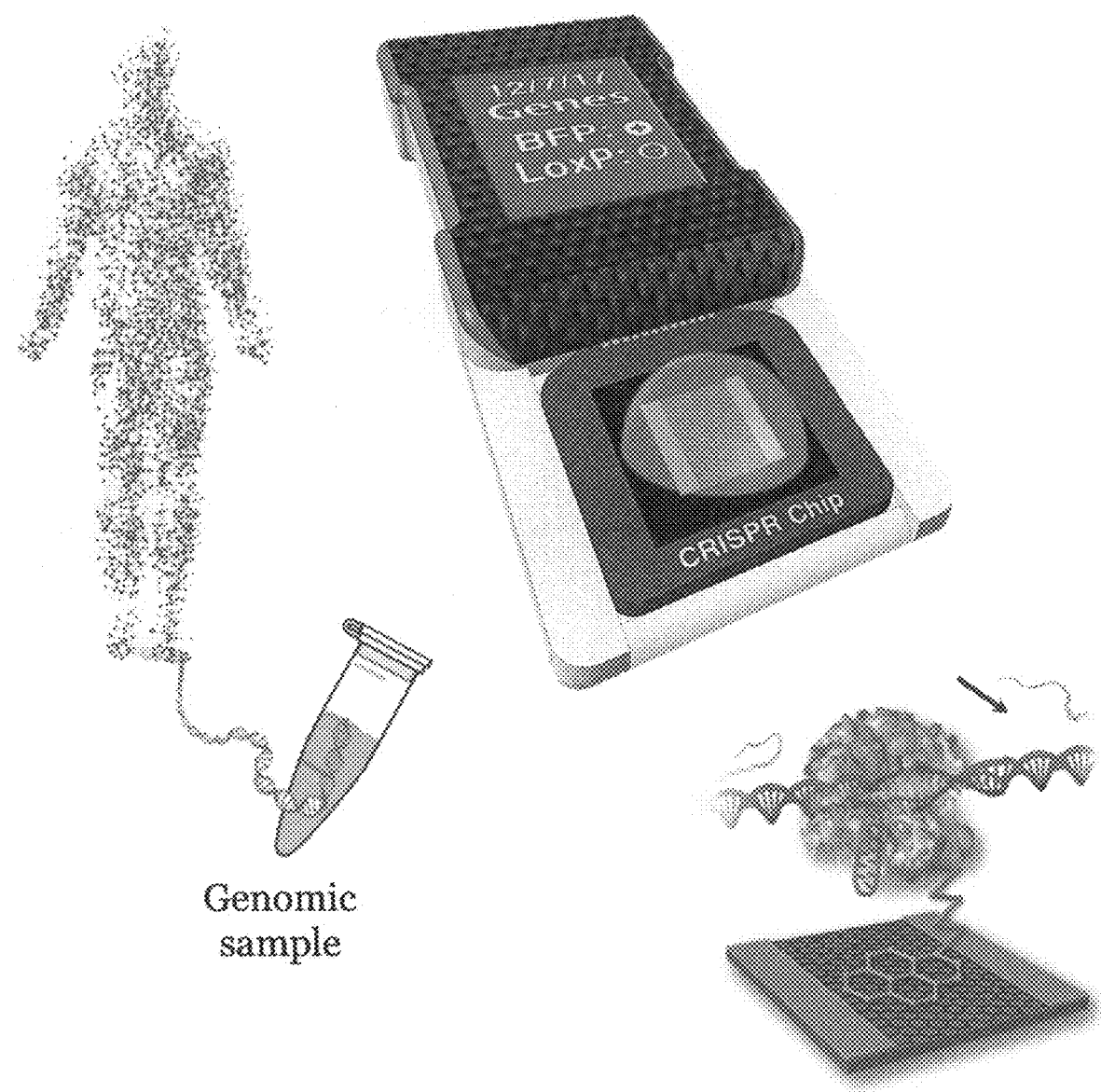
FIG. 1A depicts an exemplary biosensor functionalized with a ribonucleoprotein (RNP) complexed with a guide ribonucleic acid (gRNA) on a graphene field-effect transistor (FET) biosensor (labeled "CRISPR Chip") for capturing (i.e., selectively binding) a target nucleic acid to the RNP-gRNA complex from a genomic sample, according to embodiments of the present disclosure.
Figure 1B:
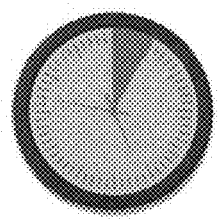
FIG. 1B shows a sample graph of the modulated electrical conductivity of graphene upon the selective binding of the target DNA to the RNP-gRNA complex (upper line labeled SIGNAL +) and electrical conductivity of the RNP-gRNA in the absence of any selective binding of the target DNA (lower line labeled SIGNAL: −), as measured over 20 minutes, with an output signal occurring as soon as 5 minutes, according to embodiments of the present disclosure.
Figure 1B:
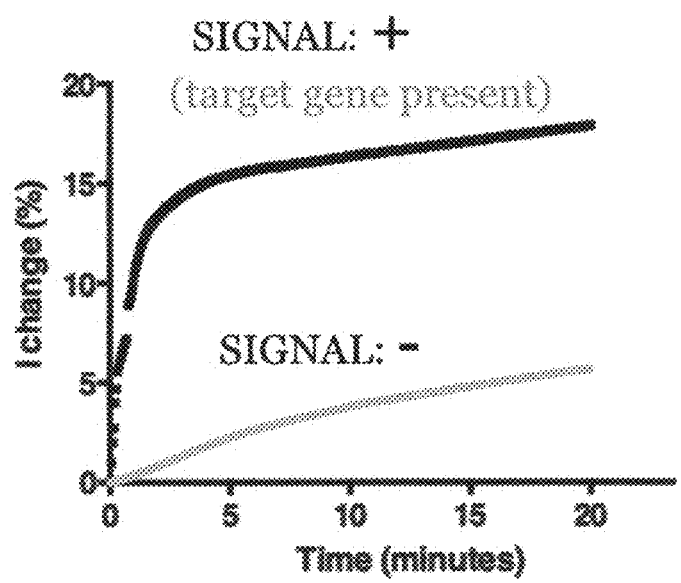

Aspects of the present disclosure are directed to a biosensor capable of digitally detecting a target nucleic acid from a whole genomic sample in the absence of amplification such as the polymerase chain reaction (PCR) as depicted in FIG. 1A. The biosensor utilizes the functionality of ribonucleoproteins (RNPs) such as the CRISPR (Clustered Regularly-Interspaced Short Palindromic Repeats) Cas proteins and the Madagascar nuclease proteins. RNP proteins characteristically bind to a guide ribonucleic acid (gRNA) fragment thereby directing the RNP protein to the region of a gene having the complementary sequence to the gRNA. Using a RNP-gRNA probe complex on a biosensor allows for a measurable electrical response upon binding of the target nucleic acid to the RNP-gRNA probe. This measurable electrical response may be a change in the current (I) over time as shown in FIG. 1B.

As used herein "a biosensor of the present disclosure" refers to a biosensor having a substrate, a substrate surface, a linker capable of binding to the substrate surface and an RNP protein that is complexed with a guide RNA having a sequence complimentary to the target nucleic acid. As the biosensor of the present disclosure provides for digital detection, the biosensor substrate includes at least two electrodes. In some embodiments, a biosensor having two electrodes confers a measurable resistance upon perturbation (binding) of a target to the immobilized RNP-gRNA probe. The biosensor may utilize a transistor of 3 or 4 electrodes including a source electrode, a gate electrode, and a drain electrode. In some embodiments, the transistor is field-effect transistor (FET).

In some embodiments, the RNP-gRNA functionalized biosensor utilizes an active RNP protein. As used herein, an active RNP protein is an active enzyme capable of specifically modifying the target nucleic acid complimentary to the gRNA. For example active Cas9 protein is a nuclease capable of cleaving the target nucleic acid (e.g., genetic DNA) complimentary to the gRNA.

In some embodiments, the RNP-gRNA functionalized biosensor utilizes inactive RNP. These inactive RNP proteins may also be referred to as "dead" proteins. For example, dead Cas9 (dCas9) is inactive Cas9. For detection of a target nucleic acid using a the biosensor of the present disclosure, it is not required that the RNP is active. However, if cleavage of the target nucleic acid is desired for further analysis, it may be useful to utilize active RNP.

Figure 2A:
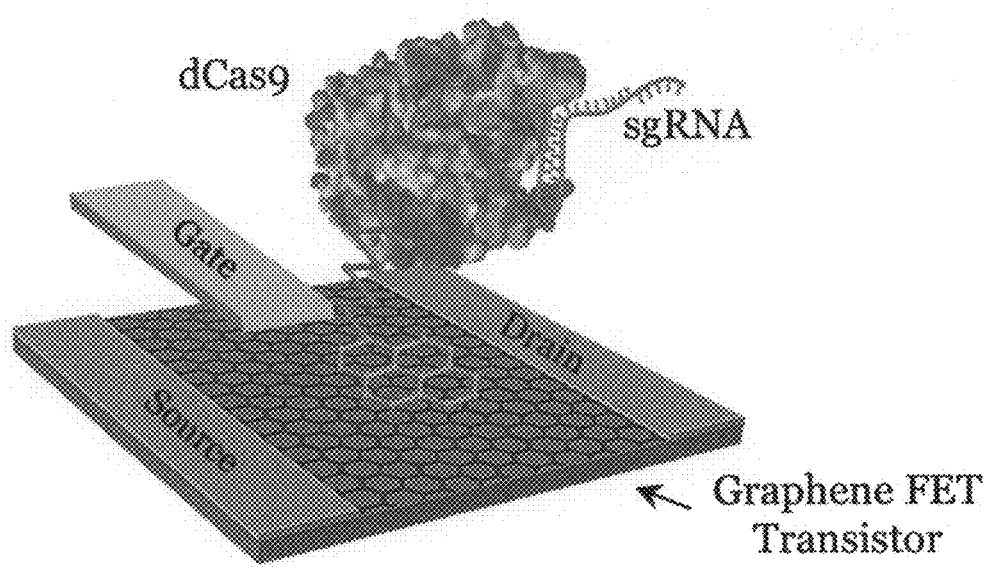
FIG. 2A is a schematic of an exemplary functionalized RNP-gRNA graphene FET biosensor depicted with each of the source, gate, and drain electrodes as indicated in which the graphene functions as a channel between the source and the drain electrodes with a liquid gate that is in contact with the sample to be tested, with the inactive RNP protein dead Cas9 (dCas9) immobilized on the graphene FET with a heterofunctional pyrenebutanoic acid (PBA) linker having a planar pyrene ring system at one end that electrostatically interacts with the p-system of graphene as shown of its hydrocarbon arm (shown in red) and a carboxylate group (shown in light blue) at the other end that covalently couples to dCas9, according to embodiments of the present disclosure.
Figure 2B:
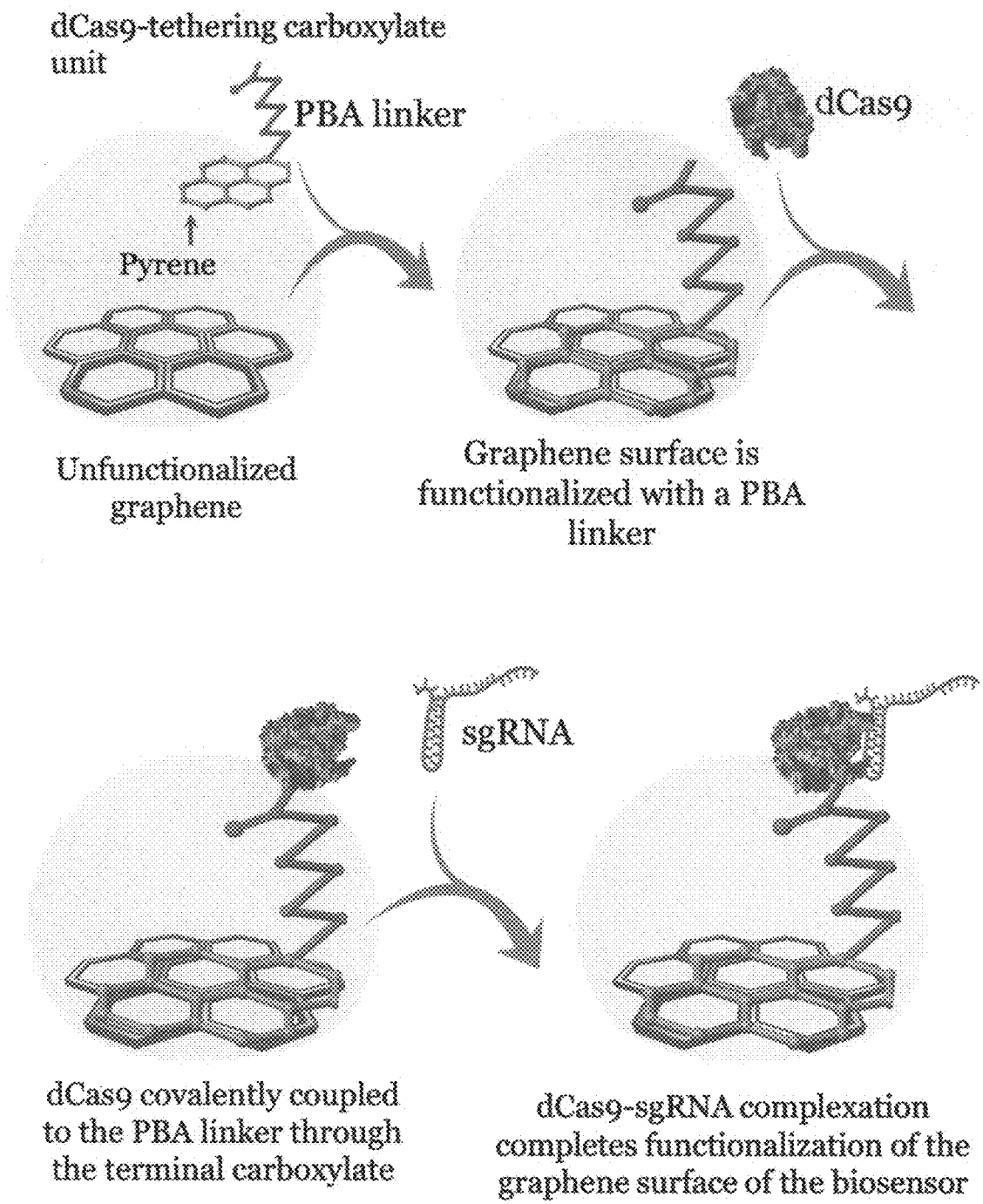
FIG. 2B is a series of schematics depicting exemplary steps for functionalizing a graphene surface with dCas9-sgRNA as described in FIG. 2A with the pyrene group of the PBA linker shown in pink, the hydrocarbon arm of PBA shown in red, and the carboxylate group shown in light blue, according to embodiments of the present disclosure.
Figure 2C:
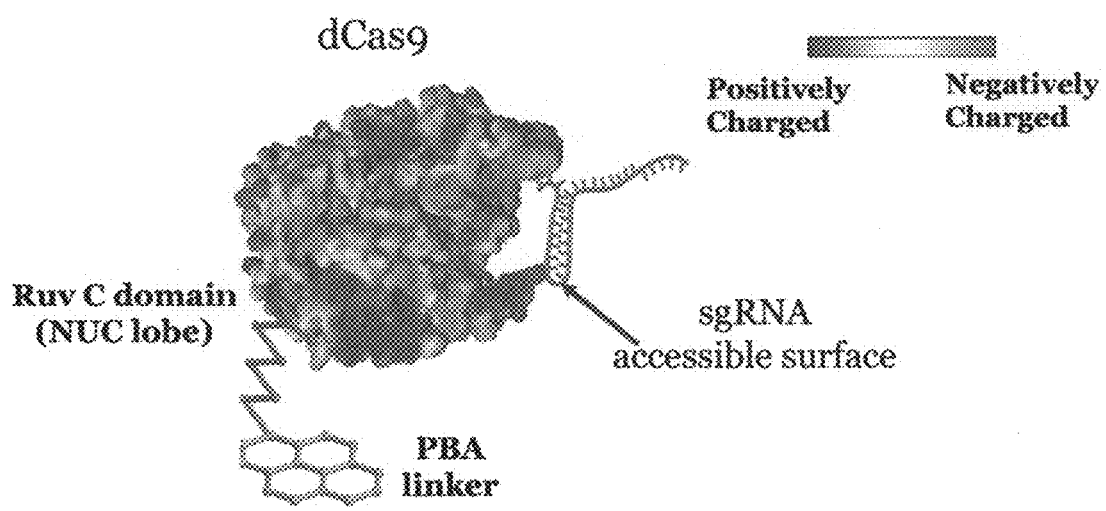
FIG. 2C is a schematic showing the electrostatic evaluation of dCas9 identified a decreased surface potential in the RuvC domain in the NUC lobe of dCas9 where positively charged surfaces are shown in blue and negatively charged surfaces are shown in red with a gradient therebetween and neutral surfaces shown in white, and as such the Ruv C domain is conducive for binding to the negatively charged carboxylate group of the PBA linker without hindering the interaction of the dCas9 protein with sgRNA, according to embodiments of the present disclosure.

The biosensor of the present disclosure includes a substrate on which the RNP protein is immobilized on the substrate such that the RNP protein maintains its ability to bind to a guide ribonucleic acid (gRNA). The RNP is immobilized (e.g., tethered or bound to) the surface of the substrate (also referred to as the substrate surface). Any suitable linker molecule may be used to immobilize the RNP protein to the substrate surface. A linker molecule has a first moiety capable of binding to the substrate surface and a second moiety capable of binding to the RNP protein without precluding the RNP binding to a gRNA. For example, as shown in FIGS. 2A-2C, if the RNP is Cas9, the substrate may be graphene and the linker may be pyrenebutanoic acid (PBA) having a first moiety of pyrene rings that bind to graphene and a second moiety of a carboxylate group that binds to the Cas9 protein in the Ruv C domain of the Nuc lobe thereby not interfering with the gRNA binding domain on the Cas9 protein. Additional linkers for the functionalization of graphene are disclosed, for example, in Georgakilas et al., *Chem Rev.* 2012, 112: 6156-6214, the entire content of which is incorporated herein by reference.

In addition to graphene, a substrate surface may include silicone, germanene, graphene nanoribbons (GNR), bilayer graphene (BLG), phosphorene, stanine, graphene oxide, reduced graphene, fluorographene, $MoS_2$, gold, or carbon. Additionally materials are disclosed for example in Schwierz, "2D Materials Beyond Graphene For Future Electronics" Apr. 15, 2015 (www.tu-ilmenau.de), the entire content of which is herein incorporated by reference.

An example biosensor of the present disclosure is the "CRISPR-Chip" as described more specifically in this disclosure. The "CRISPR Chip" is combines the gene-targeting capacity of CRISPR with the highly sensitive sensing power of a graphene-based field effect biosensors (gFEB) to afford the rapid and ultra-sensitive detection of a target gene contained within intact genomic DNA. The sophisticated gene-targeting capacity of CRISPR-Cas9 (CRISPR-associated nuclease) protein, was incorporated into CRISPR-Chip, to replace the conventional double primer system required for many molecular diagnostics. In contrast to gene-targeting primer pairs, the CRISPR-Cas system only requires the nuclease-guiding single strand RNA of the ribonucleic complex to be tuned to target a desired gene of interest.

CRISPR-Chip exploits the gene-targeting capacity of CRISPR-Cas9 to enable highly selective detection of a gene target, by incorporating the CRISPRS-dCas9 (dCas9 complexed to a designed sgRNA) onto the surface of a graphene field-effect biosensor. The dCas9-sgRNA complex scans whole genomic DNA until it identifies its target sequence (complementary to sgRNA), unzips the double helix, and kinetically binds to the the DNA target. The selective binding event of the target DNA to the dCas9-sgRNA complex modulates the electrical conductivity of graphene to afford a detectable signal output in less than 5 min.

Complexation of the sgRNA to dCas9 affords the functional gene-targeting dCas9-sgRNA unit and completes the functionalization process.

Finally, synthesized sgRNA, complementary to a gene of interest, is introduced and complexes with dCas9 tethered to the graphene surface.

CRISPR-Chip implements different single-guide RNAs (sgRNAs) complexed to nuclease "dead" Cas protein 9 (dCas9) to effectively target and bind to a desired gene loci. These gene specific ribonucleoprotein complexes comprised of a sgRNA bound as a ligand to dCas9, denoted as dRNP, gets its geneF targeting capacity from simply modifying the unique 20 nucleotide (nt) sequence at the 5'-end of the sgRNA molecule. When anchored to graphene, the CRISPR complex is sufficient for targeted DNA binding and identification without any need for amplification or complicated detection protocols, making CRISPR-Chip an innovative, portable CRISPR-powered nucleic acid testing platform closely attuned to the point of care.

CRISPR-Chip is composed of a 3-terminal graphene-based field effect transistor (FET), which utilizes graphene as a channel between the source and the drain electrodes with a liquid gate in contact with the genomic samples. The graphene channel of CRISPR-Chip is functionalized with dRNPs as the gene recognition elements for specific interaction with target sequences (FIG. 2A). The dRNP complex immobilized on the surface of the graphene in CRISPR-Chip interacts with its target sequence by scanning the whole genomic samples, unzipping the double helix and associating at the site of a Protospacer Adjacent Motif (PAM) until it finds and binds sgRNA to its complementary sequence10, 14. The binding event between the dRNP and the target gene results in a shift in the graphene conductivity and overall electrical parameter of the transistor, which can be detected in real-time.

CRISPR-Chip is constructed by first immobilizing dCas9 on the surface of the graphene channel, then by complexing the immobilized dCas9 to a designed sgRNA specific to a target gene of interest (FIG. 2B). Briefly, a molecular linker, 1-pyrenebutanoic acid (PBA), is non-covalently anchored onto the surface of the graphene. The pyrene base of the PBA linker binds to the graphene surface through π-π non-covalent bonds.

The carboxylic acid head of the PBA linker is then chemically activated such that it can covalently bind with a primary amine using carbodiimide crosslinking chemistry. dCas9 is then introduced onto the surface of the graphene chip, where its primary amines readily couple with the electrostatically anchored PBA to form a covalent carbodiimide tether, which effectively immobilizes the dCas9 protein onto the graphene surface. Lastly, a sgRNA molecule specific to the target DNA is introduced onto the surface of graphene to form the dRNPs. This method of dCas9 immobilization and dRNPs formation was shown to not affect the ability of the complexed sgRNA to interact with its complementary double stranded DNA (dsDNA) target as investigated by CHARMM PBEQ-Solver and Chimera. FIG. 2D shows the electrostatic evaluation of the surface potential of dRNP which indicated that the RuvC region of dCas9, responsible for the binding of sgRNA, was not sterically hindered due to the electrostatic interaction between the negatively charged graphene surface and the positively charged regions of the dRNP. Therefore, dRNP maintains its high binding specificity and affinity to its target dsDNA upon immobilization on the graphene.

To demonstrate selectivity, CRISPR-chip was functionalized with dCas9-sgRNA (denoted with the gray sgRNA) to target the bfp gene, termed dRNP-BFP, and dRNP-PCSK9 (denoted with the red sgRNA) as a negative control, as shown in FIGS. 4A-4D, Solutions of bfp PCR product were analyzed on both the bfp-targeting CRISPR-chip (right, dRNP-BFP) and the pcsk9-targeting CRISPR-Chip (left, dRNP-PCSK9). The $I_{DS}$ response of the bfp-targeting CRISPR-Chip in the presence of the bfp PCR product was significantly higher than that generated on the pcsk9-targeting CRISPR-Chip (n=3, p<0.0001). The dRNP-BFP CRISPR-Chip detected its target dsDNA in 2.5 min. Additionally, the rate of current change is greater for more concentrated samples (1800 ng bfp) compared to the less concentrated sample (900 ng bfp).

Figure 5A:
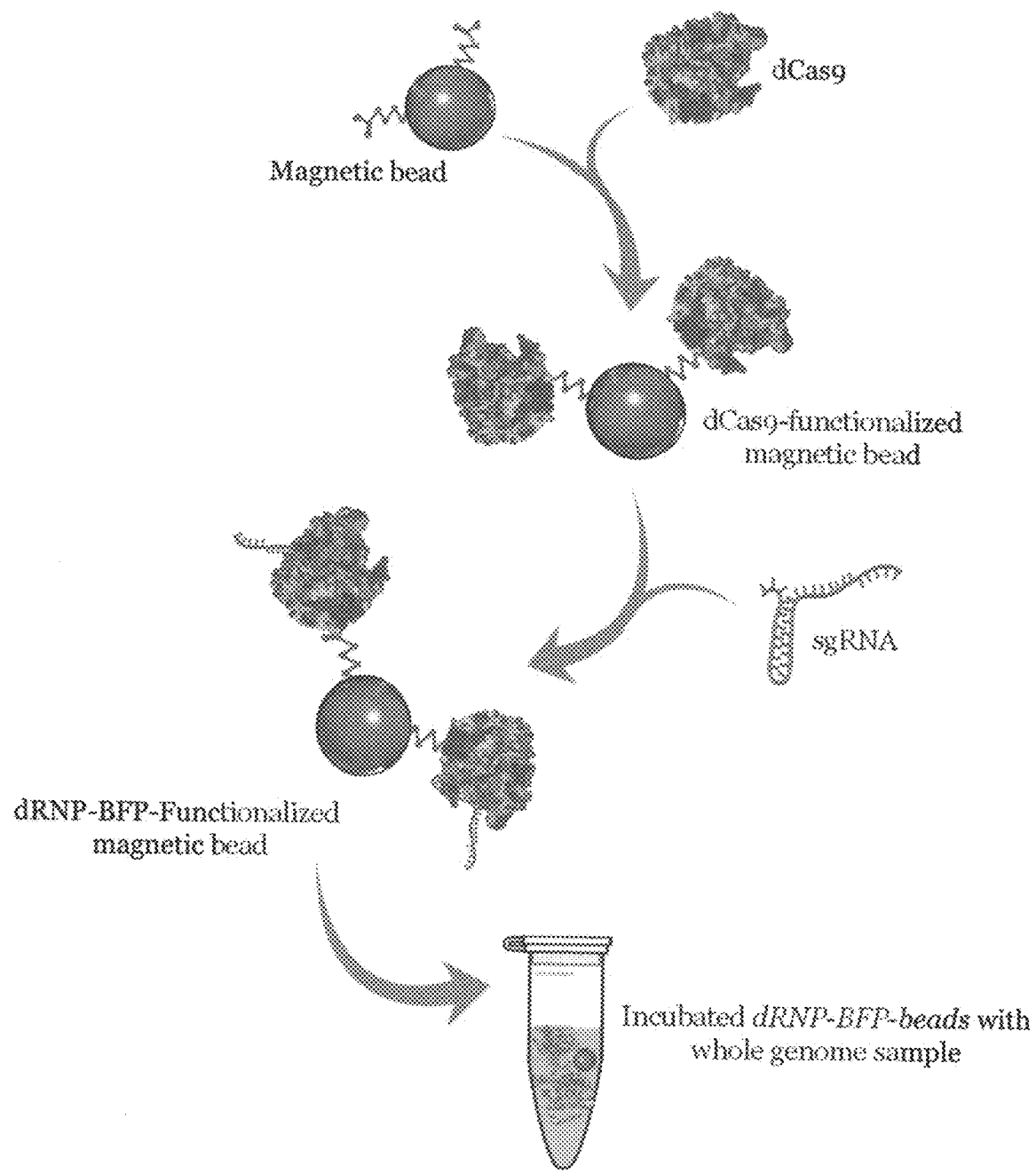
FIG. 5A is a schematic depicting an RNP-functionalized magnetic bead used to evaluate the binding capacity of the dRNP for its target gene, in which the RNP is first covalently attached to the surface of the magnetic bead and then the RNP bead is incubated with a sgRNA-BFP that is complementary to the bfp gene target to form the RNP-BFP functionalized magnetic bead which is then incubated with a genomic sample according to embodiments of the present disclosure.
Figure 5B:
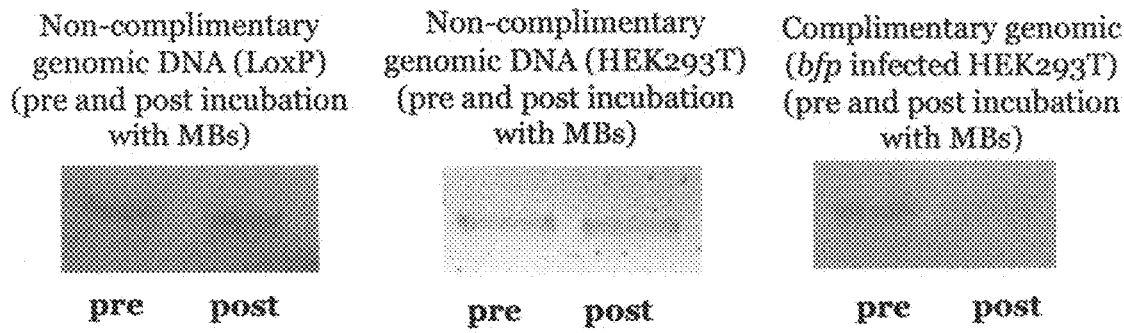
FIG. 5B is a gel electrophoresis of the RNP-BFP functionalized magnetic beads showing the amount of genomic bfp in the indicated genomic suspensions before (pre) and after (post) incubation with nonspecific mouse genomic DNA (LoxP) (n=3), noncomplementary human genomic material HEK293T cells(n=3), or specific human genomic material (bfp-infected HEK293T cells) (n=4) that was captured by the RNP-BFP beads, according to embodiments of the present disclosure.
Figure 5C:
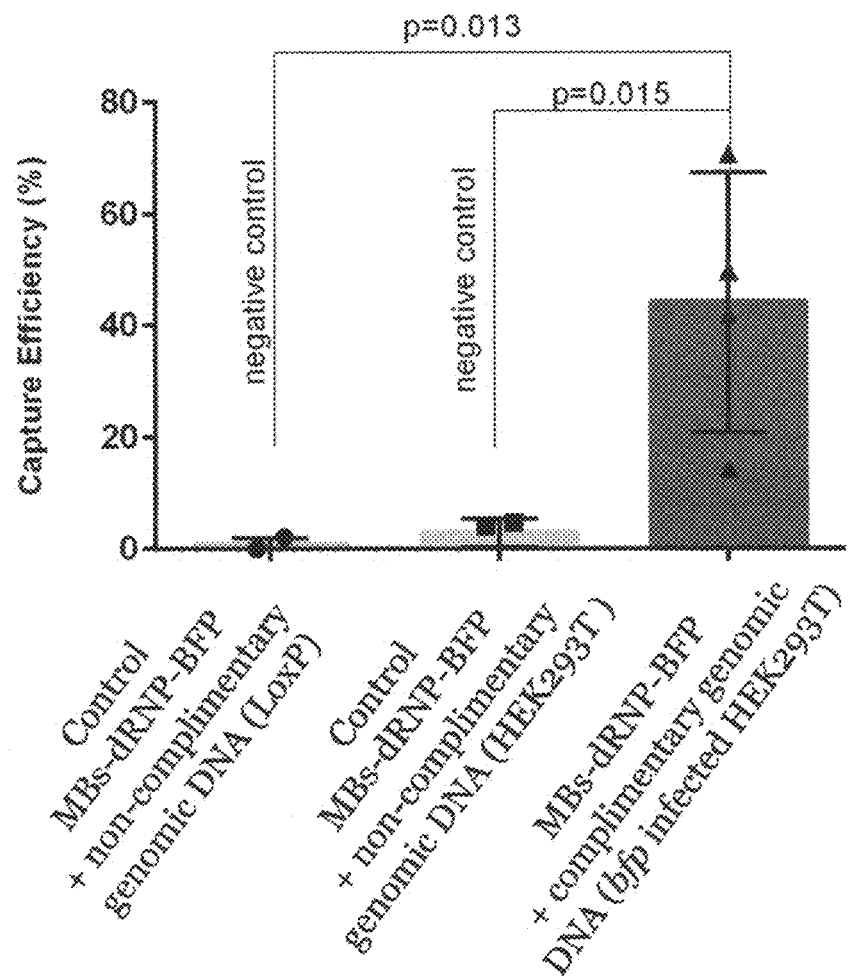
FIG. 5C is a graph of each of the genomic samples in FIG. 5B in which the amount of genomic bfp in each sample after incubation with RNP-BFP functionalized magnetic beads was quantified relative to the amount of genomic bfp before incubation to determine a Capture Efficiency (%) of bfp for each sample, where the dRNP-BFP beads captured about 40% of the total genomic bfp according to embodiments of the present disclosure.

A CRISPR-functionalized magnetic bead was synthesized to evaluate the binding capacity of the dRNP for its target gene a shown in FIGS. 5A-5C. The CRISPR-functionalized magnetic bead was produced by first covalently attaching dCas9 to the magnetic bead surface, then incubating with sgRNA-BFP, complementary to the bfp gene target. Finally, 20 ng genomic material was incubated with the functional CRISPR-beads for 30 minutes at 37° C. The capture affinity of the bfp-targeting CRISPR-beads was evaluated by gel electrophoresis to determine the amount of nonspecific mouse genomic LoxP (n=3), noncomplimentary human genomic material (n=3), or specific human genomic material containing bfp (n=4) was captured by the CRISPR-bead. The dRNP-BFP was able to bind and maintain its target genomic material and extract approximately 40% of the genomic BFP, dark grey column in the plot.

The following Examples are presented for illustrative purposes only, and do not limit the scope or content of the present application.

EXAMPLES

Example 1

Figure 7:
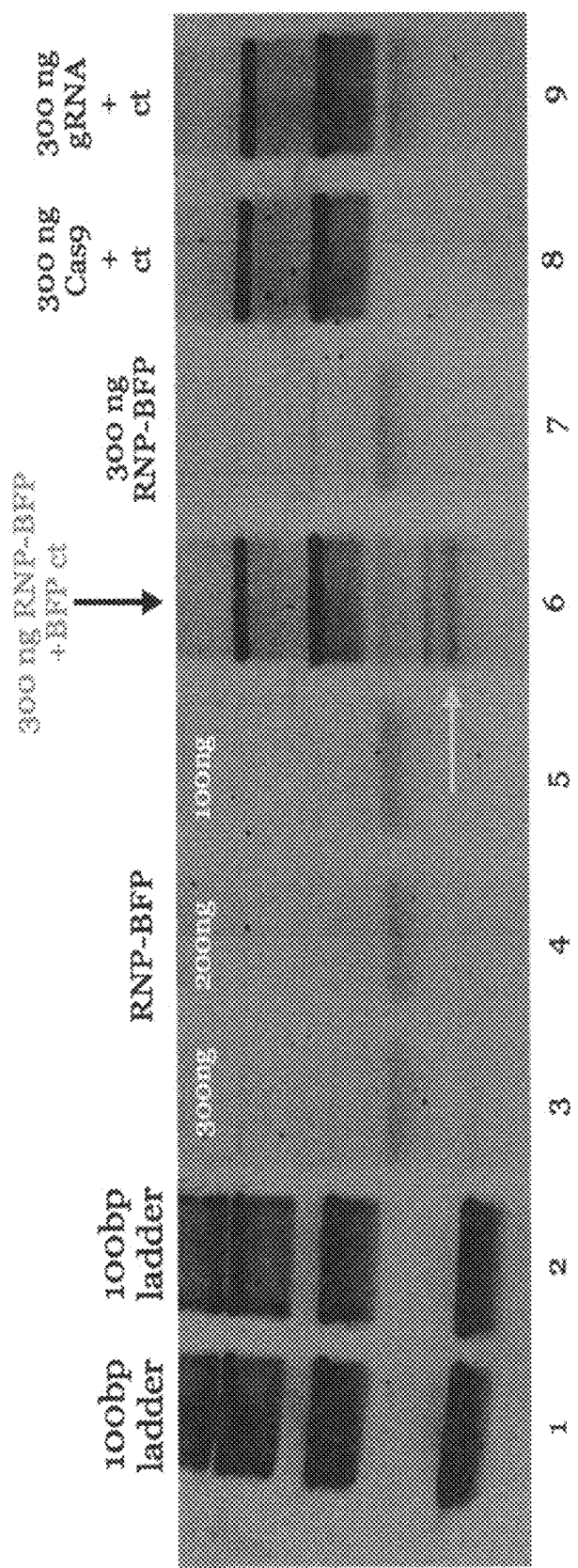
FIG. 7 is a polyacrylamide gel electrophoresis (PAGE) gel validating the bfp gene-targeting of sgRNA-BFP), where lanes 1 and 2 contain 100 bp DNA ladder standards; control lanes 3-5 contain RNP-BFP complex prepared by incubating Cas9 with 100 ng, 200 ng, or 300 ng of sgRNA-BFP; lane 6 contains the active RNP with its bfp gene target (denoted +bfp-ct), and control lanes 7 and 8 where bfp-ct was incubated with either sgRNA-BFP or Cas9, in which new bands are only observed in lane 6, where the bfp target gene was incubated with the active RNP-BFP, indicating cleavage of bfp-ct, and that content of each sample shown in lanes 3 through 9 was incubated at 37° C. for 12 hours prior to being loaded onto the PAGE gel (120V for 45 minutes) and then stained with SYBR™ Safe DNA stain for 30 min prior to imaging, according to embodiments of the present disclosure.
Figure 8:
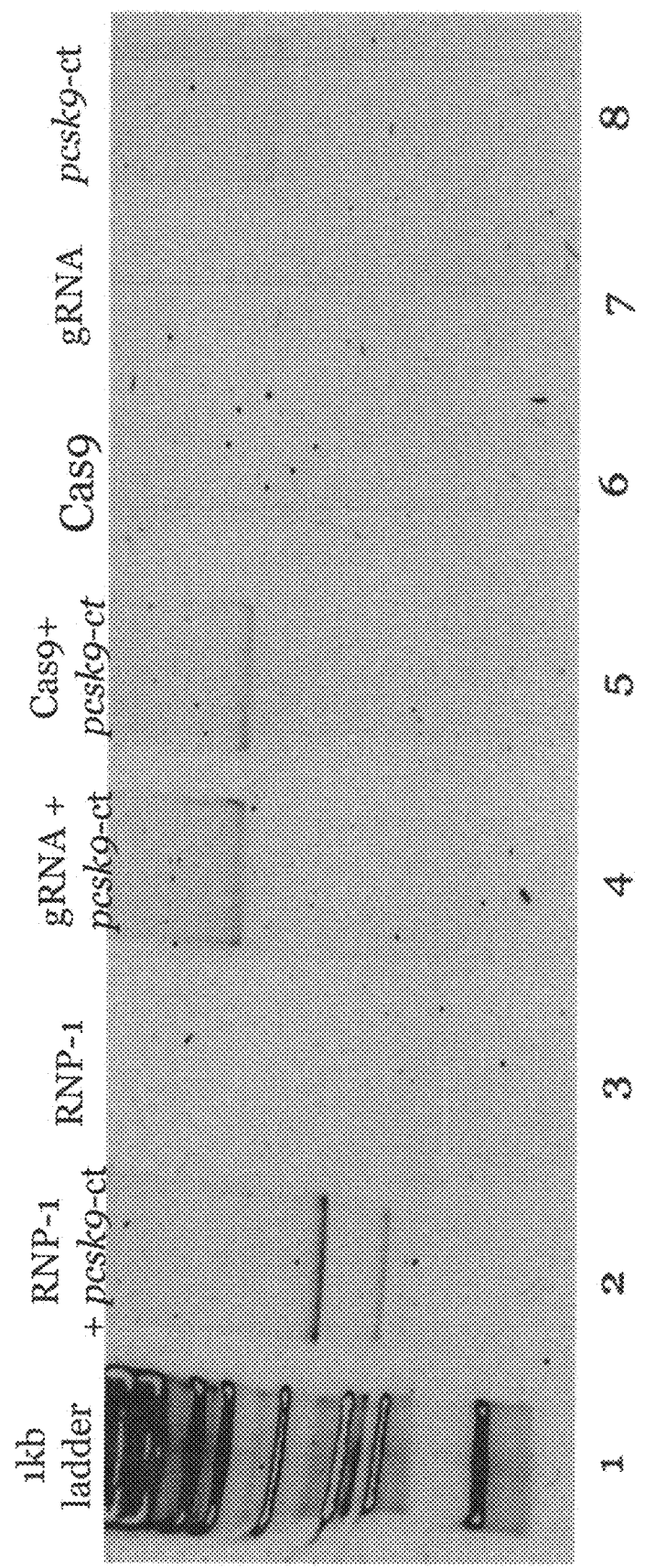
FIG. 8 is a PAGE gel validating the pcsk9 gene-targeting sgRNA (gRNA-1), where lane 1 a contains 1 kilobase (Kb) DNA ladder standard; lane 2 contains the active RNP-1 with its pcsk9 gene target (denoted pcsk9-ct); control lane 3 contains only RNP-1, which was prepared by incubating gRNA-1 with Cas9; lanes 4 and 5 contain samples where pcsk9-ct was incubated with gRNA-1 or Cas9; lanes 6 and 7 contain only gRNA-1 or Cas9, and lane 7 contains only pcsk9-ct where only new bands are observed in lane 2 in which the pcsk9 target gene was incubated with the active RNP-1, indicating cleavage of pcsk9-ct, where the content of each sample shown in lanes 2 through 8 was incubated at 37° C. for 1 hour prior to being loaded onto the PAGE gel (120V for 45 minutes) and then stained with SYBR™ Gold nucleic acid stain for 20 minutes prior to imaging, according to embodiments of the present disclosure.
Figure 9A:
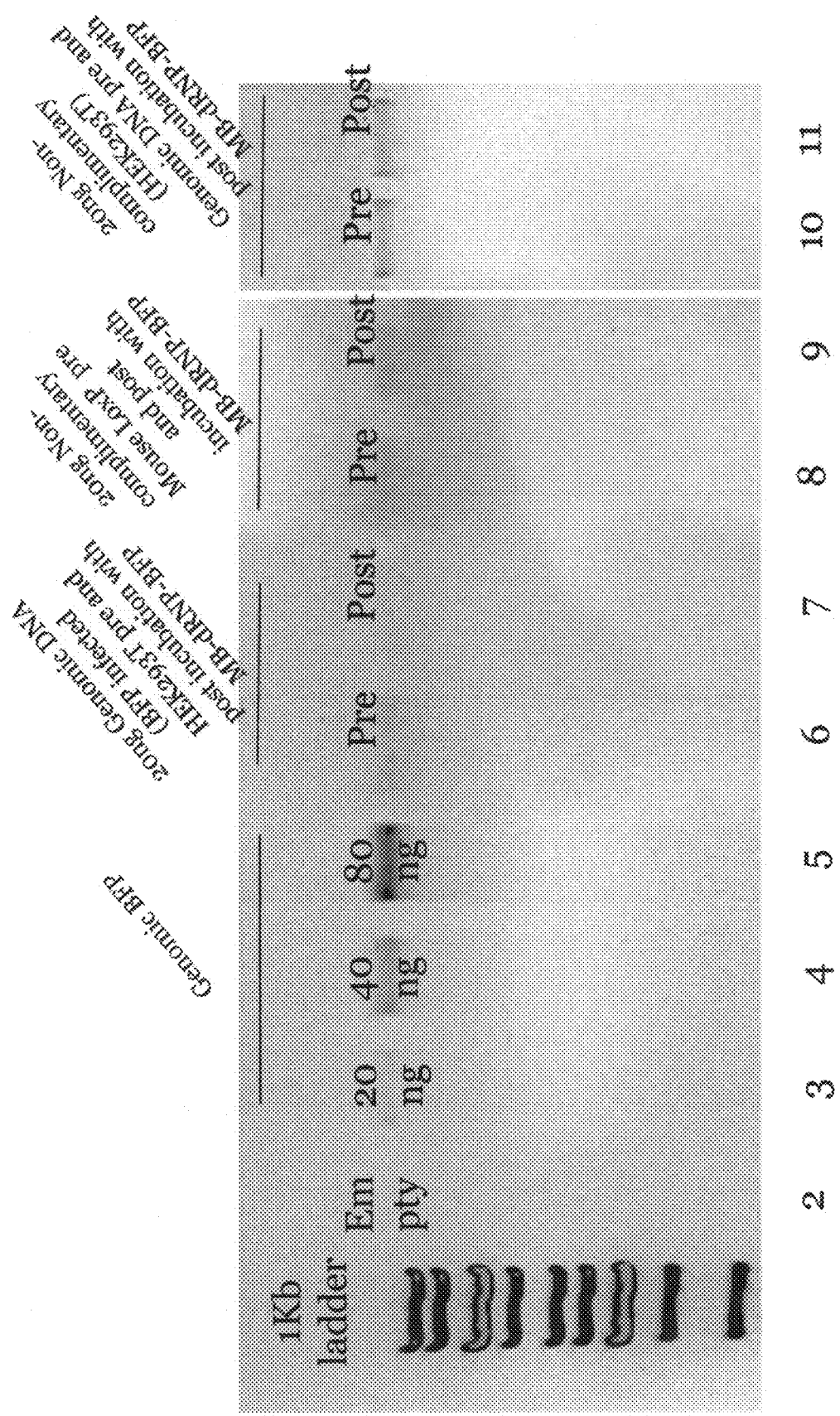
FIG. 9A-9B are each a PAGE gel analysis to evaluate MB-dRNP-BFP capture efficiency in the presence of genomic DNA with and without bfp gene target in which the PAGE gel validates the affinity of MB-dRNP-BFP for its gene target, where lane 1 shows a 1Kb DNA ladder standard, lane 2 is empty, lane 3, 4, and 5 contain 20 ng, 40 ng, and 80 ng of genomic BFP respectively; lane 6 contains 20 ng of a genomic sample including the bfp gene (pre incubation with MB-dRNP-BFP), lane 7 contains 20 ng of genomic sample including the bfp gene post incubation with 3.3 µg/µl MB-dRNP-BFP, lane 8 contains 20 ng of non-complimentary genomic LoxP (pre incubation with MB-dRNP-BFP), lane 9 contains 20 ng non-complimentary genomic LoxP post incubation with 3.3 µg/µl MB-dRNP-BFP, lane 10 contains 20 ng HEK293T non-complimentary genomic DNA (pre incubation with MB-dRNP-BFP), and lane 11 contains 20 ng non-complimentary HEK293T genomic DNA post incubation with 3.3 µg/µl MB-dRNP-BFP, where the gel ran for 1.5 hours at 100V and was imaged after a 30 minute incubation with ethidium bromide, according to embodiments of the present disclosure.
Figure 9B:
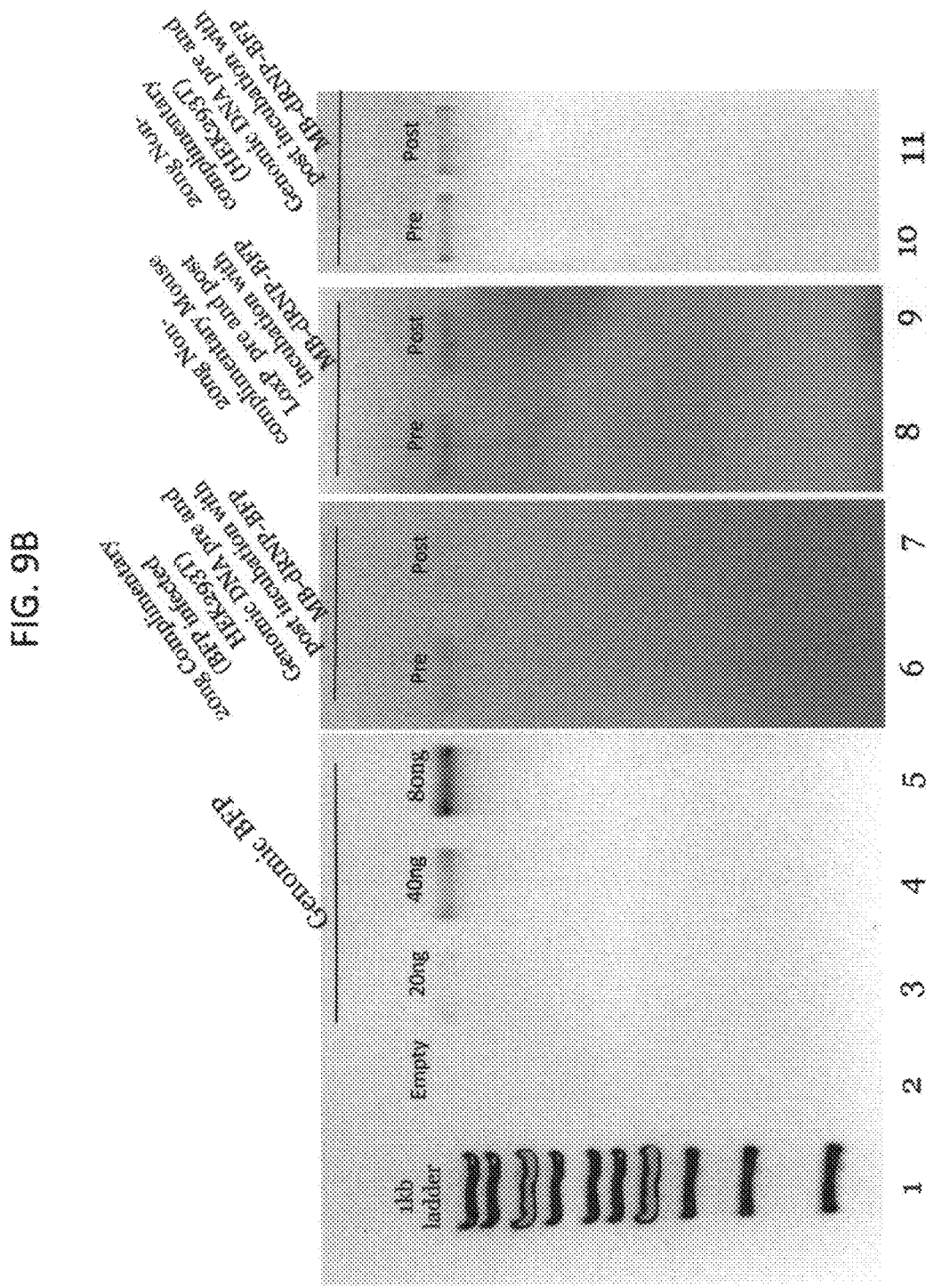
Figure 10:
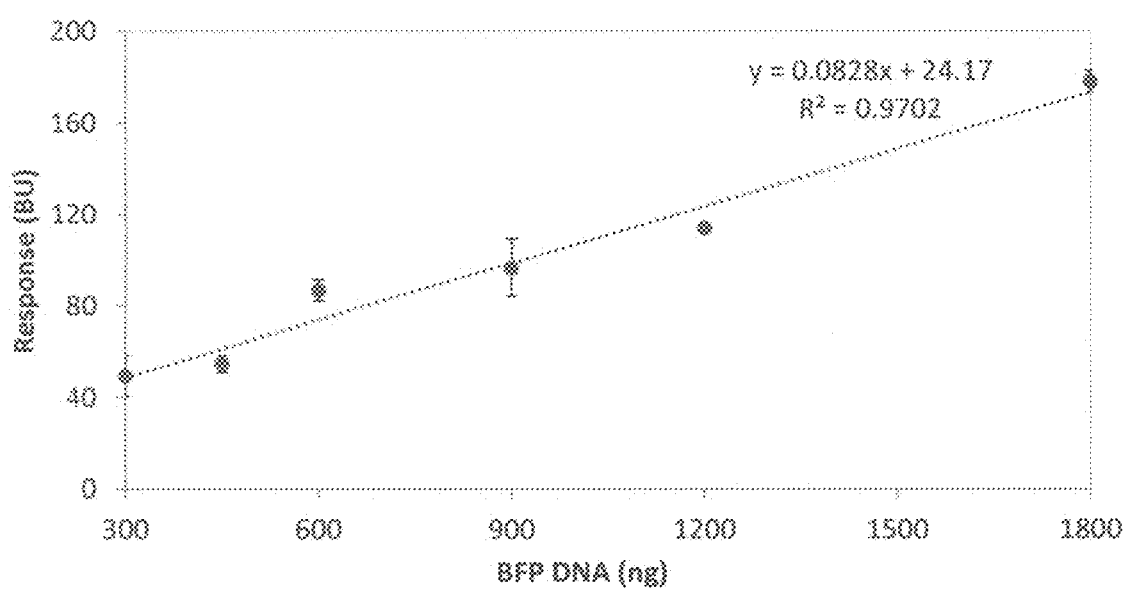
FIG. 10 is a calibration curve measuring the electric Response (BU) measured from a graphene FET biosensor functionalized with dCas9-gRNA targeting the bfp gene in the presence of bfp DNA in the range of 300 ng to 1800 ng with 2 mM $MgCl_2$ on the biosensor where dCas9 is provided at 900 ng and the bfp-gRNA is at 900 ng and the incubation occurs at 37° C., where the calibration curve shows a linear relationship between the amount of bfp present in the sample and the electric response readings from the biosensor, according to embodiments of the present disclosure.
Figure 11:
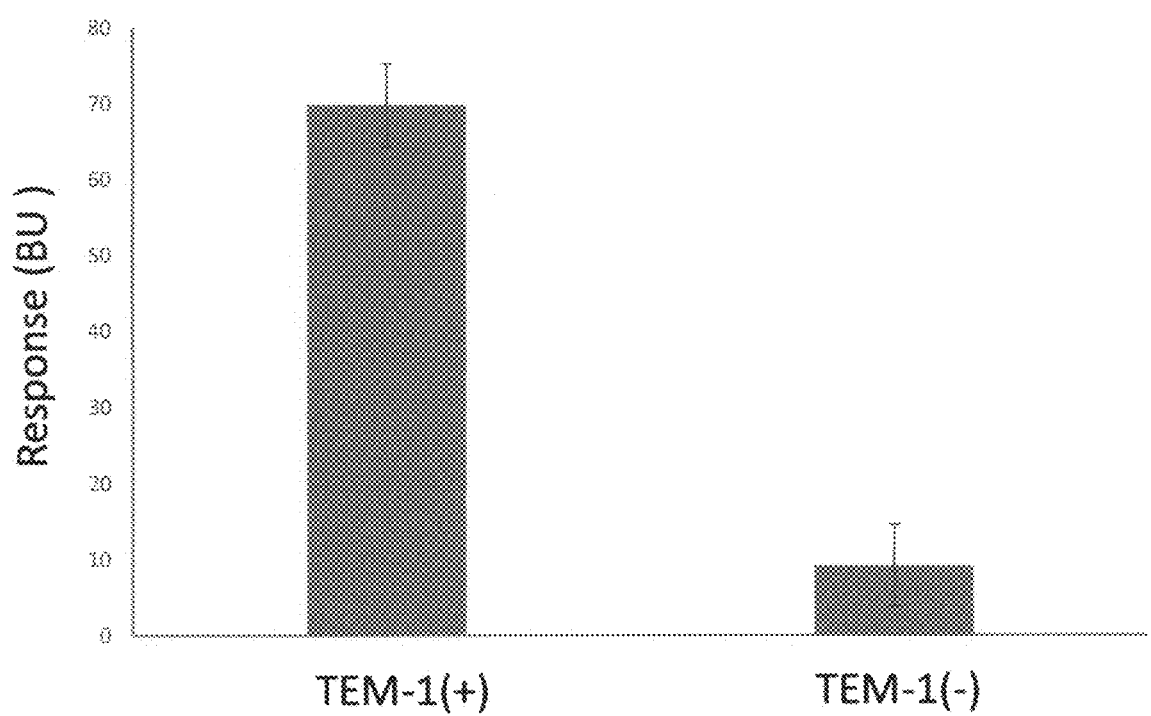
FIG. 11 is a graph showing the average electrical Response of three urine sample from three different human subjects known to be positive for the TEM-1 antibiotic resistance gene (indicated as TEM-1(+)) and three urine samples from three different human subjects known to be negative for the TEM-1 gene (indicated as TEM-1(−)) in which each of the samples were incubated on a graphene FET biosensor functionalized with dCas9-gRNA-TEM-1, according to embodiments of the present disclosure.
Figure 12:
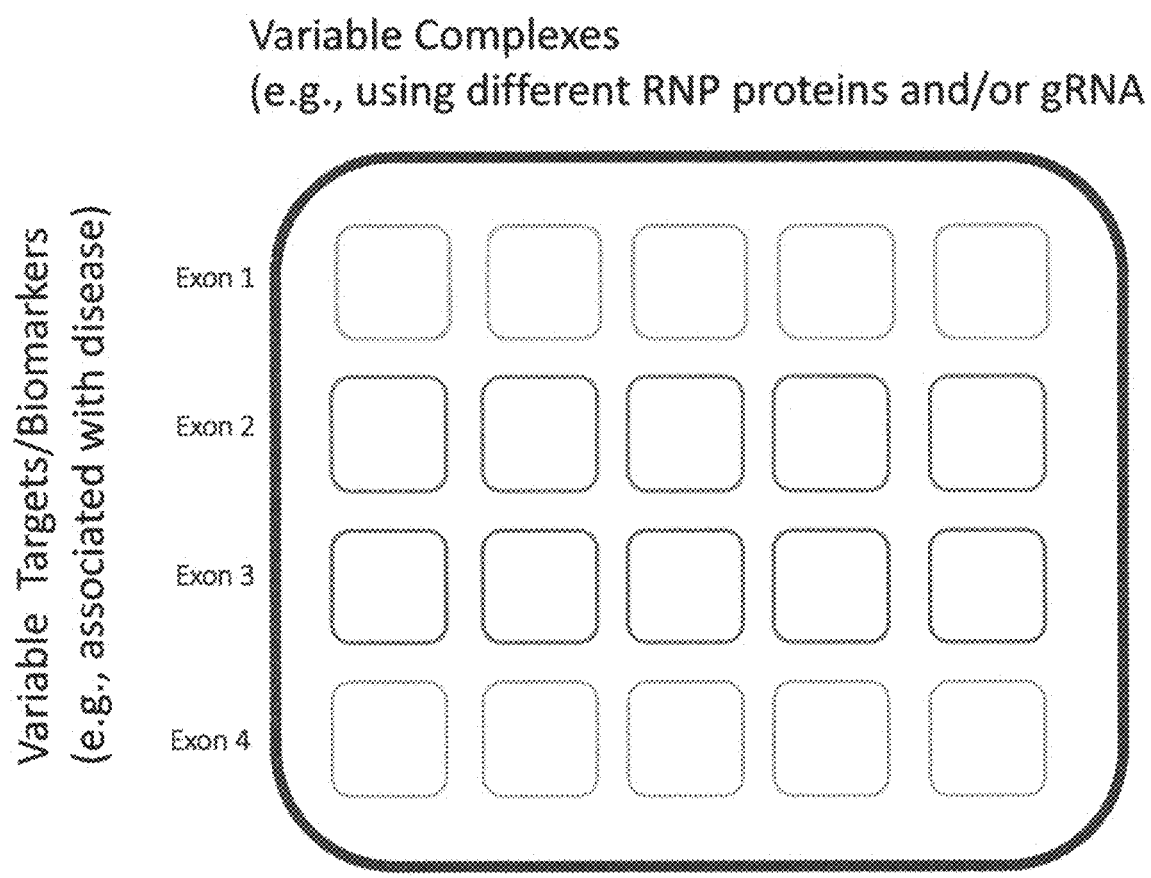
FIG. 12 depicts an exemplary multiplex RNP-sRNA biosensor capable of assaying different targets (e.g., disease biomarkers) which may be in the form of the amplified DNA product corresponding to the biomarker (e.g., mutation or variant) in which 4 different biomarker DNA products (Exon 1, Exon 2, Exon 3, and Exon 4) are possible in the example multiplex biosensor shown, and various RNP proteins and/or different gRNA probes may be assayed for each biomarker DNA product in order to identify an RNP-gRNA pair having the highest affinity and selectivity for a particular biomarker target, according to embodiments of the present disclosure.

Specificity of the functionalized dCas9-gRNA graphene FET biosensor (also referred to herein as the "CRISPR-Chip") was shown to be specific to the immobilized target dsDNA by introducing two model genes onto the surface of the graphene. The two model genes used were pcsk9 which encodes for protein PCSK9 (protein convertase subtilisin/kexin type 9) and has been associated with cardiovascular disease by contributing to elevated low-density lipoprotein levels and bfp which encodes for BFP (blue fluorescent protein) and is engineered by transfection of HEK293T cells with a BFP-containing lentivirus. To functionalize CRISPR-Chip, sgRNAs specific to pcsk9 and bfp were designed and validated. Validation was carried using gel electrophoresis and active Cas9 complexed with designed sgRNAs to ensure that the successful cleavage of gene targets took place which confirm sgRNAs efficiency and specificity to their target dsDNA as shown in FIGS. 7 and 8.

Figure 3A:
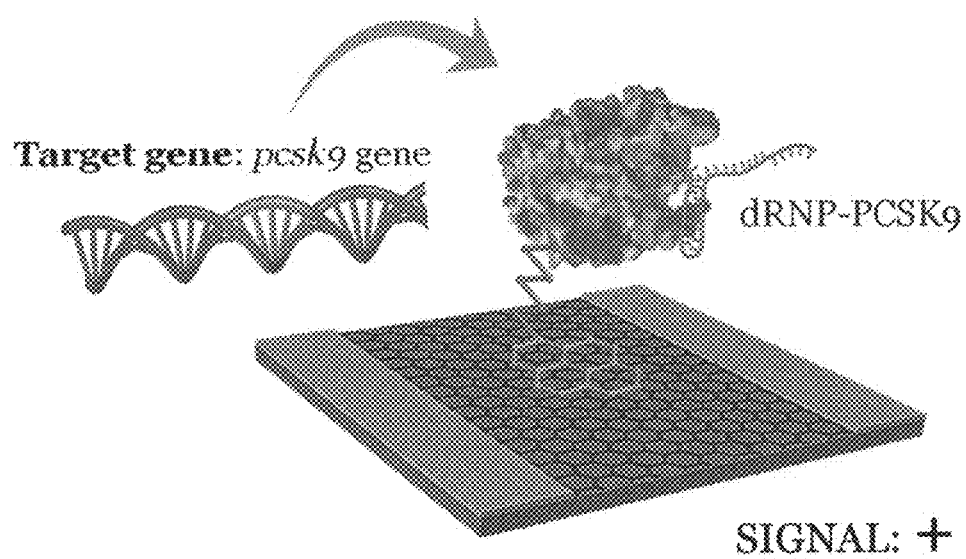
FIG. 3A is a schematic depicting a graphene FET biosensor functionalized with a dRNP-PCSK9 complex as shown where the sgRNA targets the pcsk9 gene (2,085 basepairs (bp)) in which the functionalized biosensor is incubated with a pcsk9 product amplified by PCR (shown in pale red), in which a strong signal output was generated (+) in the presence of the pcsk9 PCR product, according to embodiments of the present disclosure.
Figure 3B:
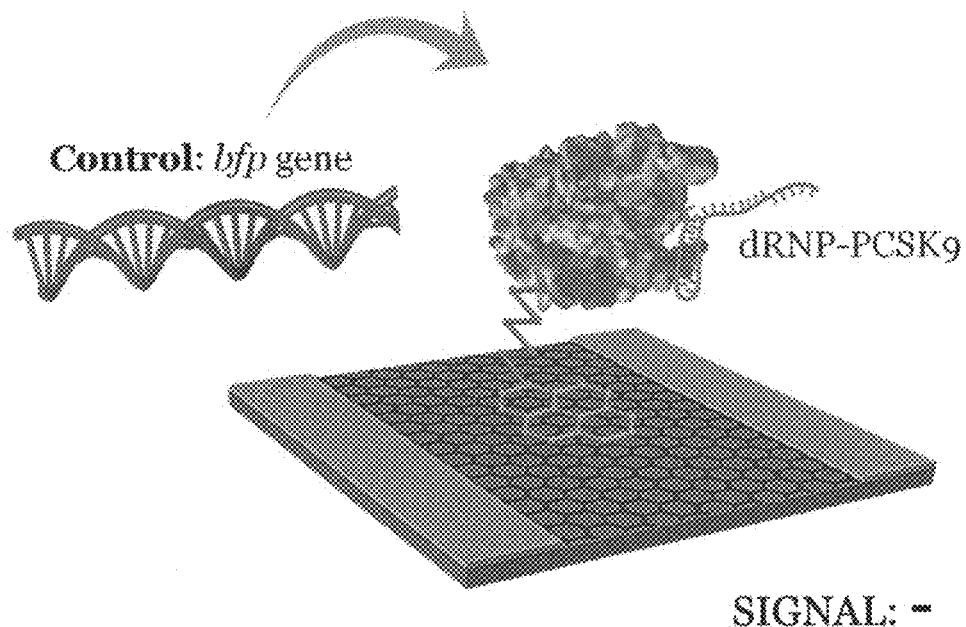
FIG. 3B is a schematic depicting a graphene FET biosensor functionalized with a dRNP-PCSK9 complex as shown where the sgRNA targets the pcsk9 gene as in FIG. 3A and the functionalized biosensor is incubated with a control bfp (blue fluorescent protein) PCR product (shown in grey), in which a weak signal output was generated (−) in the presence of the bfp PCR product, according to embodiments of the present disclosure.
Figure 3C:
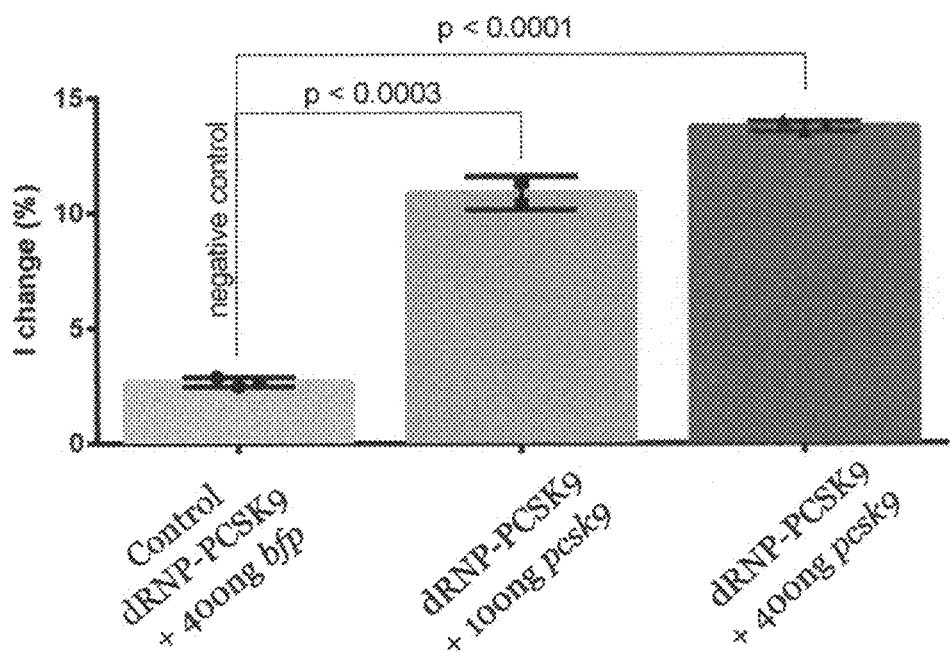
FIG. 3C is a graph of the percent change of current (I change (%)) as measured using the dRNP-PCSK9 functionalized graphene biosensor after incubation for 20 minutes with 100 ng or 400 ng of pcsk9 PCR or 400 ng of bfp PCR product as indicated, according to embodiments of the present disclosure.

After successful sgRNA design and validation, biosensor CRISPR-Chips were functionalized with dRNPs specific to pcsk9 (dRNP-PCSK9) as disclosed herein and schematically shown in FIGS. 2A-2B. Once functionalized, the biosensor chips were calibrated using MgCl2 buffer for 5 minutes. MgCl$_2$ was chosen to calibrate the chip as this buffer was also used to prepare all the genetic material. This CRISPR-Chip biosensor functionalized with dRNP-PCSK9 was then incubated with 100 ng and 400 ng of pcsk9 PCR products (FIG. 3A). For the negative control, identically functionalized chips were incubated with 400 ng of bfp PCR product (FIG. 3B). FIG. 3C shows the change in sensor current between the source and drain ($I_{ds}$) response of CRISPR-Chip functionalized with dRNP-PCSK9 after exposure to pcsk9 or bfp PCR products. The normalized change in current between the current upon pcsk9 or bfp binding and the current prior to the addition of target was used to calculate the percent current response change according to the following equation:

$$I \text{ change} = (I_{ds} - I_{ds0})/I_{ds0} \tag{1}$$

Where $I_{ds}$ is the current obtained from CRISPR-Chip in the presence of pcsk9 or bfp PCR products, and $I_{ds0}$ is the current prior to exposure to the target molecule during sensor calibration.

Figure 3D:
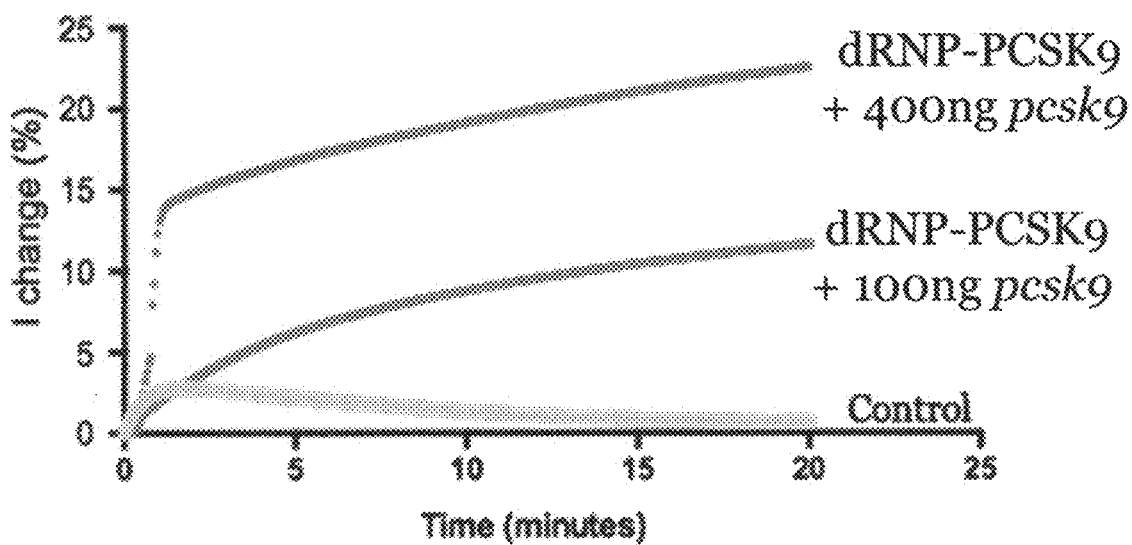
FIG. 3D is a graph of the percent change of current (I change (%)) over time (in minutes) as measured using the dRNP-PCSK9 functionalized graphene biosensor in the presence of 100 ng or 400 ng pcsk9 PCR product, according to embodiments of the present disclosure.

The results from these experiments indicated that the CRISPR-Chip current change in the presence of the target gene (pcsk9) was significantly larger than that of the non-target bfp gene (p<0.0003). There was a 14% and 11° A change in CRISPR-Chip current after exposure to 400 ng and 100 ng of pcsk9 PCR product, respectively, as compared to 2.5% change in the CRISPR-Chip current after exposure to bfp PCR product indicated that CRISPR-Chip response was specific to its target gene sequence. In addition, the real-time monitoring of CRISPR-Chip current response indicated that this CRISPR-Chip has a fast response (within 2.5 minutes) in the presence of target dsDNA (FIG. 3D).

Figure 4A:
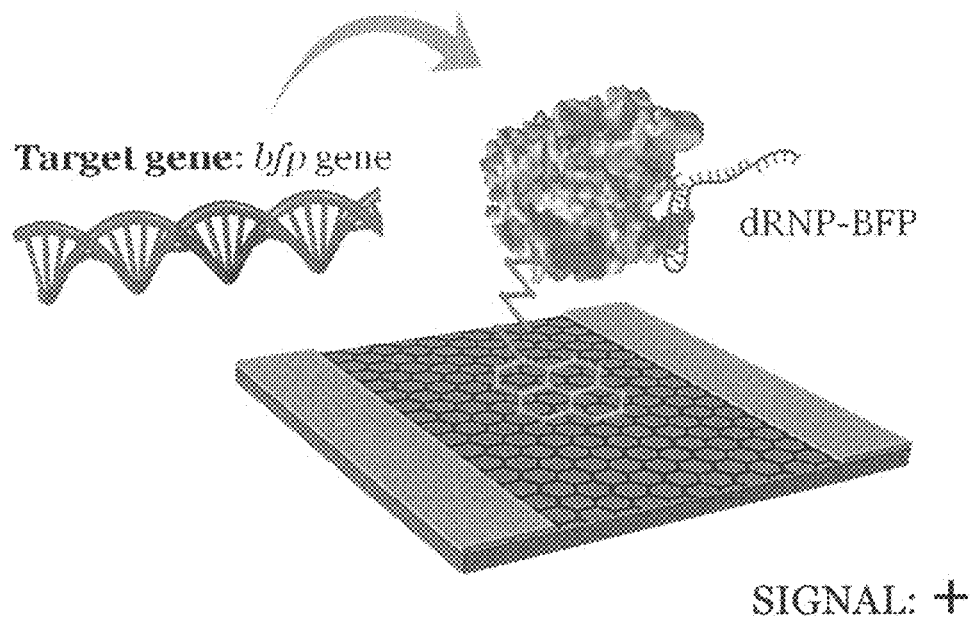
FIG. 4A is a schematic depicting a graphene FET biosensor functionalized with a dRNP-BFP complex as shown where the sgRNA targets the bfp gene in which the functionalized biosensor is incubated with a bfp product amplified by PCR (shown in grey), in which a strong signal output was generated (+) in the presence of the bfp PCR product, according to embodiments of the present disclosure.
Figure 4B:
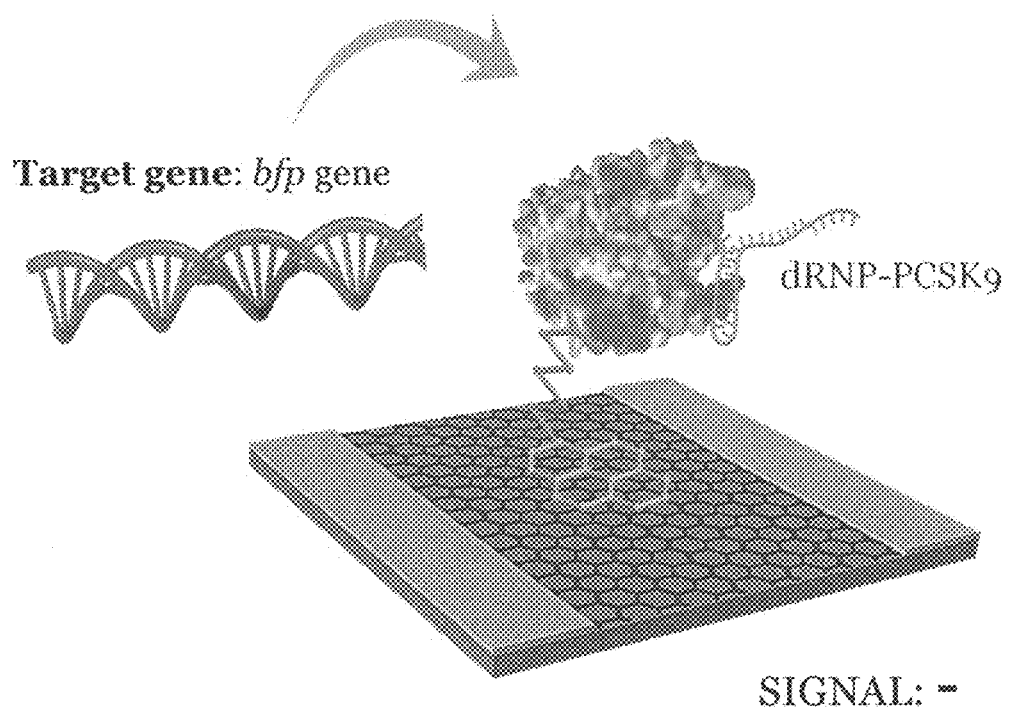
FIG. 4B is a schematic depicting a graphene FET biosensor functionalized with a control dRNP-PCSK9 complex as shown where the sgRNA targets the bfp gene and the functionalized biosensor is incubated with the bfp PCR product, in which a weak signal output was generated (−) in the presence of the bfp PCR product, according to embodiments of the present disclosure.
Figure 4C:
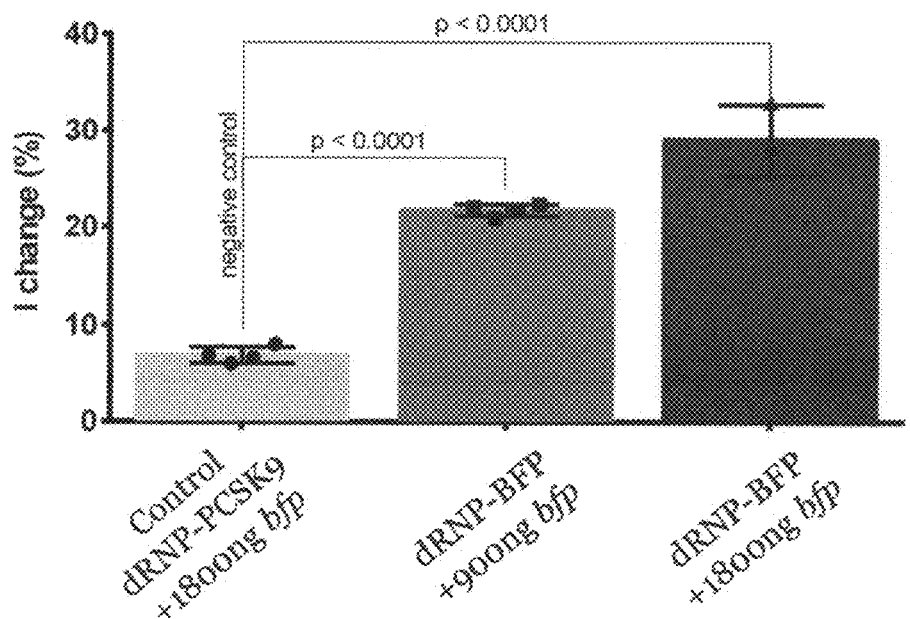
FIG. 4C is a graph of the percent change of current (I change (%)) as measured using the dRNP-BFP or dRNP-PCSK9 functionalized graphene biosensor after incubation for 20 minutes with 900 ng or 1800 ng of bfp PCR product as indicated, according to embodiments of the present disclosure.
Figure 4D:
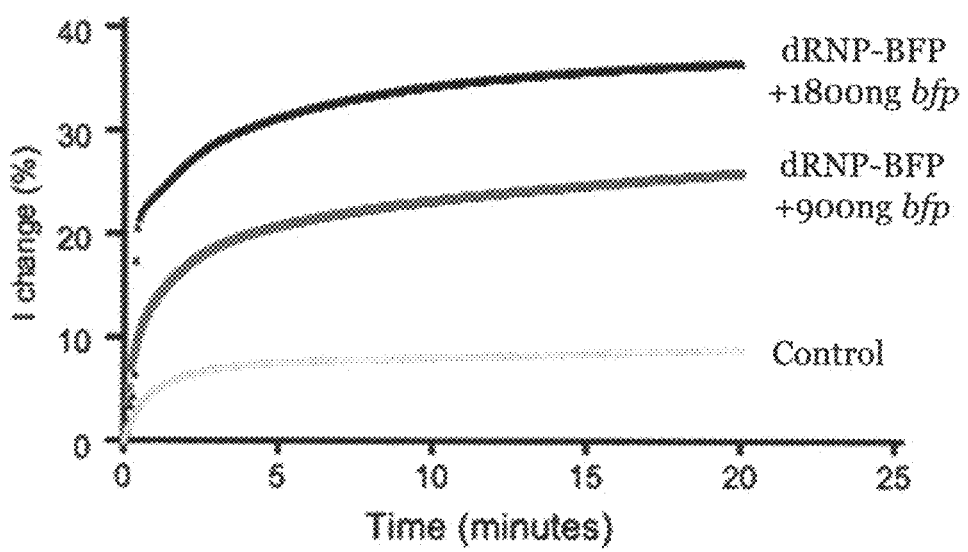
FIG. 4D is a graph of the percent change of current (I change (%)) over time (in minutes) as measured using the dRNP-BFP or the dRNP-PCSK9 functionalized graphene biosensor in the presence of 900 ng or 1800 ng bfp PCR product as indicated, according to embodiments of the present disclosure.

The specificity of the dRNPs to solely bind to their gene target was examined. For this experiment, CRISPR-Chips were functionalized with either dCas9-sgRNA specific to bfp (dRNP-BFP) or pcsk9 (dRNP-PCSK9). The CRISPR-Chips functionalized with dRNP-BFP were incubated with 900 ng and 1800 ng of bfp PCR product (FIG. 4A). For the negative control, CRISPR-Chips functionalized with dRNP-PCSK9 were incubated with 1800 ng bfp PCR product (FIG. 4B). The results from this experiment indicate that the sensor current change in the presence of the target gene (bfp) was highly specific to immobilized dRNPs-BFP and was significantly larger than that of the nonspecific dRNPs-PCSK9 (p<0.0001) (FIG. 4C). The 30% and 20% change in dRNP-BFP functionalized CRISPR-Chip current after exposure to 1800 ng and 900 ng of bfp PCR product, respectively, as compared to 6% change in dRNP-PCSK9 functionalized CRISPR-chip current after exposure to 1800 ng of bfp PCR product indicated that CRISPR-chip response is specific to the immobilized dRNP. Furthermore, the real-time monitoring of the CRISPR-Chip response as shown in FIG. 4D, also demonstrated the fast response time (within 2.5 minutes) of the CRISPR-Chip in the presence of target specific dRNPs and target dsDNA.

Example 2

Detection of target nucleic acids from genomic samples. The ultimate goal of the CRISPR-Chip is the ability to detect its target dsDNA from whole genome samples without gene amplification. To do so, it was ensured that the immobilized dRNPs are capable of binding and maintaining their affinity to the target sequences within the scale of whole genome samples. Therefore, experiments were performed to evaluate the capture efficiency of the immobilized dRNPs when exposed to unprocessed target genomic samples. For these experiments, the dRNPs-BFP were immobilized on the surface of carboxylated magnetic beads (MBs) (Invitrogen, 2.5 µm) with a protocol similar to that of CRISPR-Chip functionalization as depicted in FIG. 5A. As shown, dCas9 was covalently bound to the carboxylated MBs via carbodiimide crosslinking chemistry. The designed sgRNA specific to bfp was then introduced to form the dRNP-BFP complex on the surface of the MBs. The ability of the functionalized MBs to extract their target sample contained in full scale genomic samples (unamplified BFP whole genome obtained from cell lysate) was used to evaluate the affinity of dRNPs to the whole genome. The functionalized MBs (1.7 µg/µl) were incubated (30 minutes at 37° C.) with 20 ng genomic BFP. As controls, functionalized MBs were also incubated with 20 ng of non-complementary genomic material extracted from HEK293T human cells and 20 ng of another nonspecific mouse genomic material (LoxP gene obtained from MetRSL274G mice). Using a magnetic separator MBs were pulled out of the solution post incubation.

The supernatant, which contained any unbound genomic material, was then extracted and evaluated using gel electrophoresis. The concentration of the genomic material was evaluated pre and post incubation to determine capture efficiency of the MBs and the affinity of the immobilized dRNPs to their target DNA within the whole genome. FIG. 5B demonstrates that the capture efficiency of the functionalized MBs for BFP genomic samples (far right panel) was significantly higher (13-fold, p=0.015) than that of the negative controls. Accordingly, the interaction between dRNPs and their target sequences within the full scale genomic DNA was maintained during the physical force of washing and pipetting when anchored to a surface.

Figure 6A:
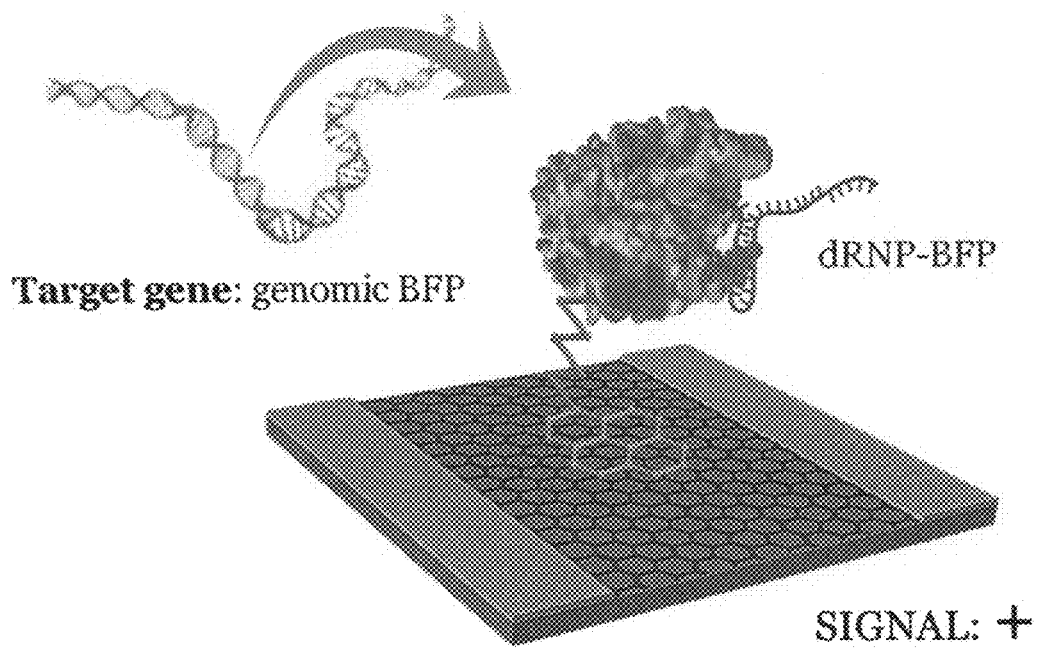
FIG. 6A is a schematic depicting a graphene FET biosensor functionalized with a dRNP-BFP complex as shown where the sgRNA targets the bfp gene in which the functionalized biosensor is incubated with a whole genomic DNA including the bfp gene in which a strong signal output was generated (+) in the presence of the whole genomic DNA including the bfp gene, according to embodiments of the present disclosure.
Figure 6B:
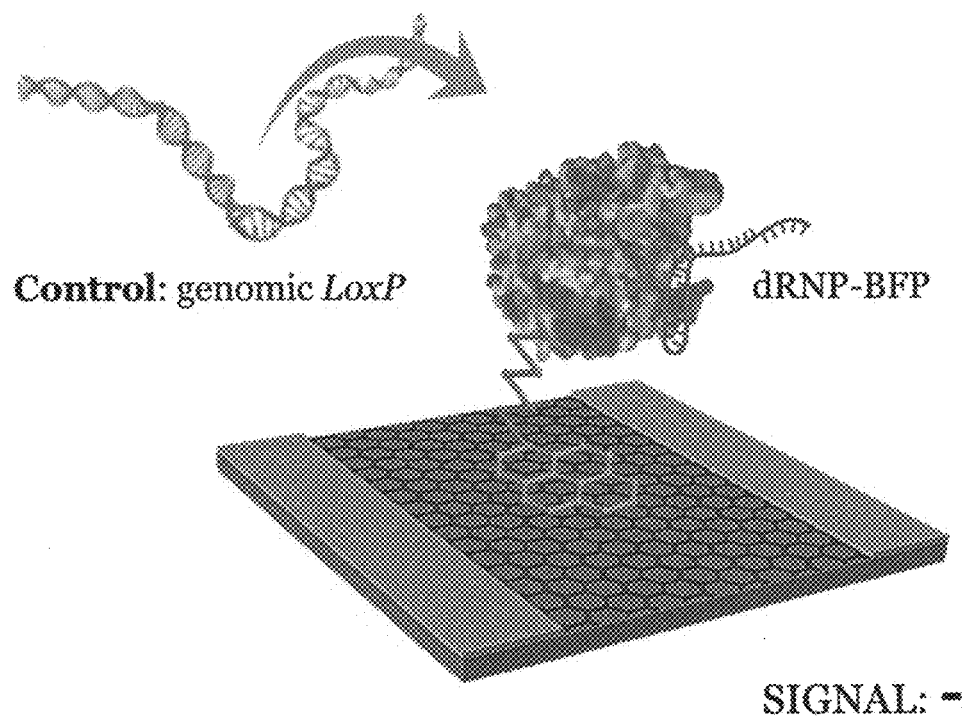
FIG. 6B is a schematic depicting a graphene FET biosensor functionalized with a dRNP-BFP complex as shown where the sgRNA targets the bfp gene in which the functionalized biosensor is incubated with a whole genomic DNA including the LoxP gene which does not include the bfp gene, in which a weak signal output was generated (−) in the presence of the whole genomic DNA including the LoxP gene, according to embodiments of the present disclosure.
Figure 6C:
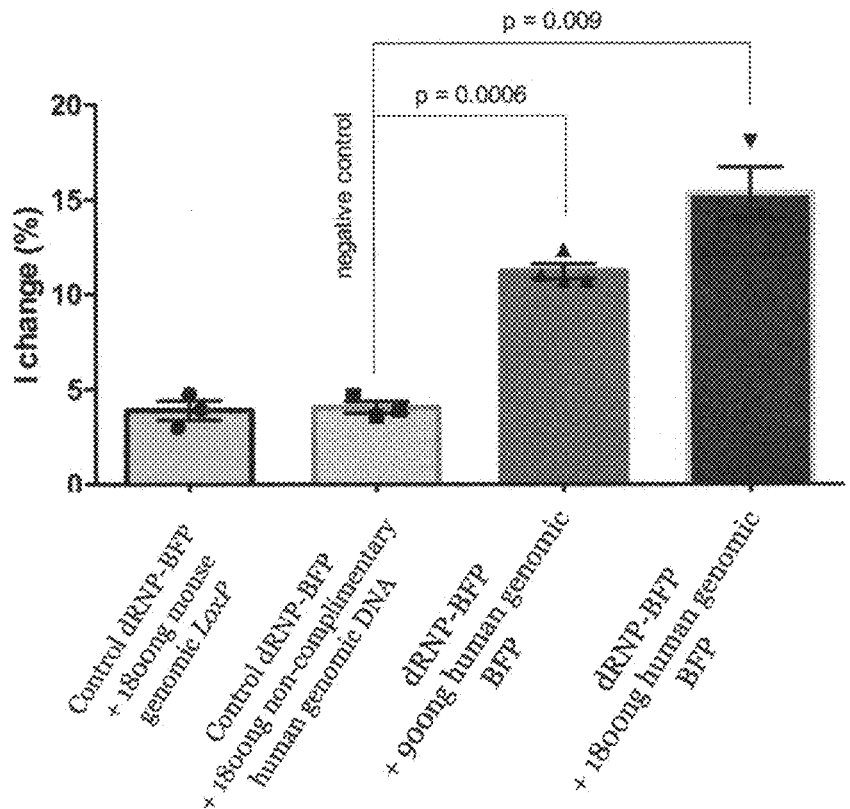
FIG. 6C is a graph showing that the percent change of the current ($I_{DS}$) in the bfp-targeting dRNP-BFP graphene FET biosensor in the presence of genomic material that contains the target bfp gene was significantly higher (p=0.009) than the percent change of the $I_{DS}$ response generated in the presence of genomic material lacking the complementary gene target (human genomic material or mouse loxP genomic material, as indicated), according to embodiments of the present disclosure.
Figure 6D:
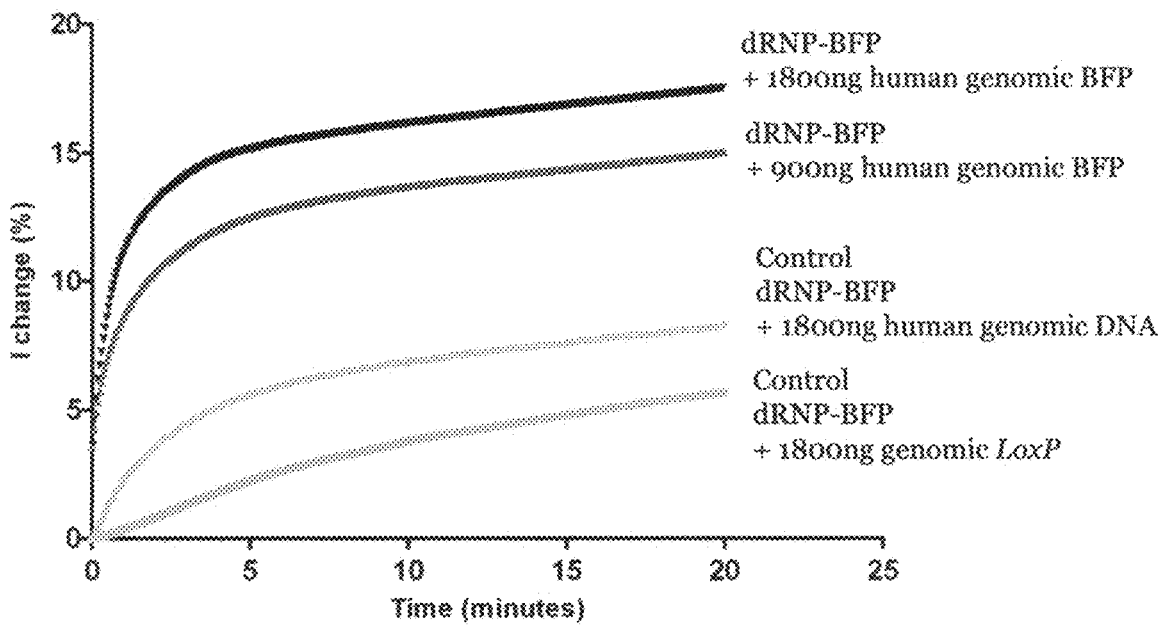
FIG. 6D is a graph of the percent change of current (I change (%)) over time (in minutes) or real-time monitoring of the $I_{DS}$ response which demonstrates that the bfp-targeting dRNP-BFP graphene FET biosensor is capable of detecting its target genomic dsDNA in less than 5 minutes, in the presence of 1800 ng or 900 ng of bfp-containing genomic material, as indicated, where no appreciable change in the $I_{DS}$ was observed when the bfp-targeting dRNP-BFP graphene FET biosensor analyzed genomic DNA lacking the bfp gene target, as shown, according to embodiments of the present disclosure.

By harnessing the genome screening capabilities of the dRNPs when anchored to the surface of the graphene chip, the ability of the CRISPR-Chip to detect whole genome samples containing the bfp target was assayed. The selection of this genomic BFP model was based on the experimental evidence collected from the aforementioned PCR models as shown in FIGS. 3A and 3B, which demonstrated that CRISPR-Chip was able to specifically detect bfp PCR products. To investigate the CRISPR-Chip ability to detect the bfp gene within whole genome samples, the graphene was functionalized with a dRNP-BFP and its performance was evaluated in the presence of two different concentrations (900 ng and 1800 ng) of genomic BFP (FIGS. 6A-6D). For control experiments, dRNP-BFP functionalized CRISPR-chips were incubated with 1800 ng human genomic samples extracted from HEK293T26 as well as 1800 ng of mouse genomic LoxP27. FIG. 6C shows that the CRISPR-chip generated a significant 5-fold enhancement (p=0.0012) in signal output after exposure to its target genetic material (BFP genomic samples) relative to control samples lacking the target sequence. Notably, real-time monitoring of the CRISPR-Chip consistently demonstrated fast response after exposure to its target. As shown in FIG. 6D, the CRISPR-Chip was able to detect the presence of the bfp DNA target within whole genomic samples within less than 5 minutes, which is faster than other nucleic acid testing platforms. This result indicates the presently disclosed graphene CRISPR-Chip may be used for genetic diagnostics and may improve the current diagnostic method within the point of care.

Example 3

Materials and Methods

Graphene-FET sensor fabrication. Graphene biosensor chips were obtained from a commercial foundry (Nanomedical Diagnostics, USA). The chips were fabricated in several stages using conventional microelectromechanical systems (MEMS) processing and were incorporated into a commercial field effect biosensing (FEB) chip. Briefly, Ti/Pt source, drain, and reference electrodes with corresponding bond pads were patterned on 6" silicon wafers using a liftoff processing technique. Wafers were then cleaned by piranha etching to remove all potential organic residues that could act as dopants of the final graphene devices. High quality graphene films grown on a copper foil substrate were spin coated with a poly methyl methacrylate (PMMA) support layer and then delaminated from the copper foil substrate by bubbling transfer. The graphene films were then deposited on top of the electrode-patterned wafers and thoroughly cleaned with acetone and isopropanol. Graphene sheets were then patterned to form defined channels between the source and drain electrodes using plasma-enhanced chemical vapor deposition (CVD) to deposit a silicon oxide layer over the entire wafer and reactive ion etching (RIE) to etch the graphene transistors. Two terminal electrical resistance characterization of the devices indicated a yield of >98% of functional graphene devices. The patterned graphene wafers were then diced into 9 mm×9 mm dice and each die was attached to a custom printed circuit board (PCB) package using epoxy and wire bonds made from the chip to the PCB. The circuit board were then encapsulated in epoxy leaving an open cavity over the exposed graphene transistors for biological sample placement. Data was collected using a commercial handheld reader (Nanomedical Diagnostics, USA) and the change in current was analyzed.

Guide RNA Design, Synthesis, and Evaluation pcsk9: Potential target sequences within the mouse pcsk9 gene were first identified using DNA 2.0 (now ATUM) CRISPR sgRNA Design Tool. A sgRNA containing a unique targeting sequences complementary to a gene target within exon 1 of pcsk9 (target sequence: ACAGTCAGCGGCACCCTCATAGG SEQ ID NO: 1) was synthesized as reported in literature. In short, a double-stranded DNA template (sgRNA DNA template) was amplified using overlap PCR, where a T7 single-stranded DNA molecule, containing the target sequence of the desired sgRNA, and L2 single-stranded DNA molecule, representative of the terminal sgRNA sequence, were utilized as the overlapping strands. The sequences of the single-stranded DNA strands for overlap PCR; T7: TAATACGACTCACTATAG SEQ ID NO: 2-guide target sequence-GTTTAAGAGCTATGCTGGAAAC AGCATAGCAAGTTTAAATAAGG SEQ ID NO: 3 and L2: GGATCCTAATACGACTCACTATAGGCTGAAGCACTGCACGCCGTGTTTTAGA GCTAGAAA SEQ ID NO: 4. The DNA template was then transcribed into the desired sgRNA using T7 RNA Polymerase and was purified using an Aurum Total RNA Mini Kit (Bio-Rad, USA). A model mouse pcsk9 cleavage template for in vitro cleavage assay analysis was amplified from cDNA (obtained from Sino Biological) and the products were purified (QIAquick PCR Purification kit, Qiagen, USA) and referred to as cleavage template, hereafter. Each sgRNA was validated using standard in vitro cleavage assay analysis, where folded sgRNA, active S. pygenes Cas9 (UC Berkeley Macrolab), and cleavage template were incubated at 37° C. for 1 hour. All control combinations of the three components were incubated under the same conditions in parallel. At the end of incubation, the sample solutions were analyzed by gel electrophoresis (Mini-Protean TGX Precast PAGE Gels, 4-15%, 12 well comb, 20 µl) at 200V for 20 min to confirm successful Cas9-sgRNA mediated cleavage (FIG. 8).

bfp: The target sequence within the bfp gene was identified and synthesized as described in Lee, K. et al. *Nat. Biomed. Eng.* 1, 889-901 (2017) and Cho, S. W., Kim, S., Kim, J. M. & Kim, J.-S. *Nat. Biotechnol.* 31, 230-232 (2013), the entire contents of both of which are incorporated herein by reference. The target sequences were validated using in vitro cleavage assays as described for pcsk9. The BFP genomic material was obtained by extraction of genomic DNA from BFP-HEK293T (PureLink™ Genomic DNA Extraction Kit Mini, ThermoFisher Scientific) and purified (QIAquick PCR Purification Kit, Qiagen) according to manufacturer's protocol. Subsequent amplification of the bfp gene from the genomic DNA was then performed (for bfp amplification protocol please refer to supporting protocols). In vitro cleavage assay of sgRNA-BFP was then performed. FIG. 7 shows the in vitro cleavage validation of sgRNA-BFP. The bfp specific sgRNA targeted the sequence GCTGAAGCACTGCACGCCATGG SEQ ID NO: 5.

dCas9-sgRNA (dRNP) immobilization on the graphene surface. The CRISPR-Chip graphene biosensor, fabricated as described herein was cleaned with acetone twice and deionized water (DIW) once. Subsequently, it was functionalized by first adding 1-pyrenebutanoic acid (PBA) (5 mM in dimethylformamide (DMF)) onto the graphene surface. The PBA (Sigma Aldrich) was allowed to incubate on the surface of the graphene for 2 hours at room temperature or overnight at 4° C. The surface of the graphene sensor was then rinsed twice with DMF and once with DIW and allowed to dry completely. The PBA was then activated using N-(3-Dimethylaminopropyl)-N'-ethylcarbodiimide hydrochloride (EDC) and N-hydroxysulfosuccinimide (s-NHS) as described in Everaerts et al., *J. Biomed. Mater. Res.* 85, 547-555 (2008) and Wang et al., *Langmuir* 27, 12058-12068 (2011), the entire contents of both of which are incorporated herein by reference.

After PBA linker immobilization and activation on the surface of the graphene, 900 ng of dCas9 (30 µl in 2 mM MgCl2) (UC Berkeley MacroLab) was pipetted onto the surface of the graphene and was incubated for 30 minutes at 37° C. This process was monitored continuously by measuring the CRISPR-chip change in current between the drain and the source ($I_{ds}$). Alterations in the graphene conductivity and CRISPR-Chip $I_{ds}$ ensured dCas9 immobilization on the graphene surface. Once dCas9 was immobilized, the unreacted PBA molecules were blocked using amino-PEGS-alcohol and ethanolamine hydrochloride which contained primary amine groups that rapidly reacted with any remaining unbound activated PBA molecules. After blocking, the graphene surface was washed with 2 mM MgCl2 solution and incubated until the Ids readings had stabilized. To form the dRNP complex, 900 ng of sgRNA (30 µl in 2 mM MgCl2) specific to bfp or pcsk9 was introduced onto the graphene surface and incubated for 15 minutes at 37° C. to form dRNP-BFP and dRNP-PCSK9. Since dCas9 can only bind to the sgRNA in monomer form, all sgRNA samples were thermally treated to remove dimer structure prior to incubation with the chip as described in Dang, Y. et al. *Genome Biol.* 16, 1-10 (2015), the entire content of which is incorporate herein by reference.

The chip was then washed with 2 mM $MgCl_2$ for 15 minutes to remove any unbound sgRNA. This final step resulted in full dRNP formation on the graphene surface and a ready to use CRISPR-Chip.

The immobilization method described above did not hinder the active zone of dCas9, where sgRNA binds as a ligand and interacts with its dsDNA target. This was first analyzed using CHARMM PBEQ-Solver and Chimera software to analyze the electrostatic surface potential of the dCas9-sgRNA complex and was then demonstrated by experimental data. Briefly, the RuvC region, responsible for cutting dsDNA in Cas9, had the highest probability of binding to the negatively charged PBA-activated graphene surface. However, for dCas9, the RuvC domain is inactive due to induced mutations37 and therefore serves as an ideal place for PBA binding. This was also confirmed by experimental evaluation of CRISPR-Chip, which indicated that dRNP complex remained active after immobilization.

CRISPR-Chip utilization to detect the PCR Products of pcsk9 and bfp. Experiments were designed to evaluate CRISPR-Chip ability to detect the PCR products of two model genes as preliminary positive controls to ensure that CRISPR-Chip would specifically interact with the sequence complementary to its designed sgRNA. Before DNA samples were introduced, the functionalized CRISPR-Chip was calibrated by incubation with 2 mM $MgCl_2$ for 5 minutes at 37° C. All double stranded DNA (dsDNA) solutions introduced onto CRISPR-Chip were incubated for 20 minutes at 37° C. and the change in CRISPR-Chip current was continuously monitored.

Investigating the affinity of the immobilized dCas9-sgRNA to target whole genomic sample. To ensure that the CRISPR-Chip could bind to its target sequence within a whole genome sample and maintain that interaction with whole genomic DNA samples, the binding affinity of dRNP-BFPs to target whole genome samples containing bfp was first evaluated using magnetic beads (MBs) (Invitrogen, 2.5 µm) functionalized with dRNP-BFP. Briefly, carboxylated MBs were activated using EDC and sNHS as disclosed in Wang et al. supra. Activated MBs were promptly coupled with dCas9 (33.3 ng/µl in 10 mM potassium phosphate, 0.15M NaCl). This reaction was left at room temperatures for 3 hours. After dCas9 coupling, MBs were blocked for 30 minutes at room temperature using 1.0M glycine so that any unreacted activated carboxylic acids would not interact with nucleic acid samples. The complete MB-dRNP-BFP complex was formed by incubating MBs coupled with dCas9 (33.3 ng/µl in 2 mM MgCl2) with sgRNA (30 ng/µl in 2 mM MgCl2) specific to BFP for 30 minutes at 37° C. This fully functional MB-dRNP-BFP complex was then utilized for extraction of genomic BFP from whole genome samples. Genomic BFP samples were obtained by extraction of genomic DNA from the HEK293T human model cell line (PureLink™ Genomic DNA Kit, ThermoFisher Scientific, United States) and purified (DNA Purification Kit, QIAquick, Qiagen, United States), as described in Lee et al., 2017, supra. For the bfp gene capture experiments, three separate treatments were prepared all with 20 ng of genomic material (30 µl in 2 mM MgCl2). For these experiments, genomic BFP samples were incubated with MB-dRNP-BFP (1.83 µg/µl) for 1 hour at 37° C. For control experiments 20 ng of non-complementary genomic LoxP extracted from mouse cells as well as 20 ng of non-complimentary human DNA extracted from the HEK293T cells were utilized and were incubated with MB-dRNP-BFP complex (1.83 µg/µl) for 1 hour at 37° C. After incubation, the reaction mixtures were placed on a magnetic separator for 3 minutes and the supernatant was eluted and evaluated using gel electrophoresis at 100V for 1.5 hours. All three genomic samples (20 ng) were also run without being treated with the MB-dRNP-BFP complex for reference. The intensities of the bands were then quantified using the software ImageJ (NIH) software and the capture efficiency of the MB-dRNP-BFP complex was quantified for each sample.

CRISPR-Chip Evaluation for Detection of Non-Amplified Whole Genomic BFP.

After the CRISPR-Chip was functionalized with dRNP-BFP as described above, 900 ng (30 μl in 2 mM MgCl2) and 1800 ng (30 μl in 2 mM MgCl2) of genomic BFP, obtained from whole cell lysate, were tested. Briefly, CRISPR-Chip was first calibrated using MgCl2 buffer. Then, genomic BFP was introduced onto the surface of CRISPR-Chip and its current change was continuously monitored. As controls, dRNP-BFP functionalized CRISPR-Chips were incubated with 1800 ng (30 μl in 2 mM MgCl2) of non-complementary mouse genomic LoxP and 1800 ng (30 μl in 2 mM MgCl2) of non-complementary human genomic DNA obtained from HEK293T cells. This experiment was designed in order to determine CRISPR-Chip capacity to bind to its specific sequence within whole genome samples and produce an adequate signal output.

While the present invention has been illustrated and described with reference to certain exemplary embodiments, those of ordinary skill in the art will understand that various modifications and changes may be made to the described embodiments without departing from the spirit and scope of the present invention, as defined in the following claims.

---

What is claimed is:

1. A biosensor for assaying a target nucleic acid, the biosensor comprising:
a substrate comprising a substrate surface and at least two electrodes for passing current through the substrate, wherein the substrate surface comprises graphene;
a pyrenebutanoic acid (PBA) linker molecule comprising a pyrene ring moiety and a carboxylate moiety, wherein the linker molecule is conjugated to the substrate surface via non-covalent interaction between the pyrene ring moiety and the substrate surface;
a ribonucleoprotein (RNP) conjugated to the carboxylate moiety of the linker molecule via covalent bonding, wherein the RNP comprises Cas9 protein, wherein the linker molecule is joined to the Recombination UV C (RuvC) domain of the Cas9 protein, and wherein the RNP is immobilized to the substrate surface via the linker molecule; and
a guide ribonucleic acid (gRNA) forming a portion of the RNP and comprising a first sequence capable of binding to a protein portion of the RNP and a second sequence capable of binding to the target nucleic acid,
wherein conductivity of the substrate surface is modulated upon binding of the target nucleic acid to the gRNA, thereby enabling a detectable current change for sensing the target nucleic acid.

2. The biosensor of claim 1 wherein the RNP is active or inactive.

3. The biosensor of claim 1, wherein the substrate surface further comprises silicon, germanene, graphene nanoribbons (GNR), bilayer graphene (BLG), phosphorene, stanine, graphene oxide, reduced graphene, fluorographene, $MoS_2$, gold, or carbon.

4. The biosensor of claim 1, wherein the substrate comprises a transistor comprising the at least two electrodes and the at least two electrodes comprise a source electrode, a drain electrode, and a gate electrode.

5. The biosensor of claim 4, wherein the transistor is a field-effect transistor (FET).

6. The biosensor of claim 1, wherein the pyrene ring moiety of the linker molecule is conjugated to the graphene of the substrate surface.

7. The biosensor of claim 1, further comprising an electronic controller capable of measuring a change in current on the substrate surface.

8. The biosensor of claim 1, wherein biosensor is configured such that the RNP and the gRNA forming the portion of the RNP remain attached to the substrate surface while modulating conductivity of the substrate surface upon binding of target nucleic acid to the gRNA.

9. A biosensor for assaying a target nucleic acid, the biosensor comprising:
a substrate comprising a substrate surface and at least two electrodes for passing current through the substrate, wherein the substrate surface comprises graphene;
a pyrenebutanoic acid (PBA) linker molecule comprising a pyrene ring moiety and a carboxylate moiety, wherein the linker molecule is conjugated to the substrate surface via non-covalent interaction between the pyrene ring moiety and the substrate surface; and
an immobilized RNP-gRNA probe that includes
a ribonucleoprotein (RNP) conjugated to the carboxylate moiety of the linker molecule via covalent bonding, wherein the RNP comprises inactive Cas9 protein, wherein the linker molecule is joined to the Recombination UV C (RuvC) domain of the inactive Cas9 protein, and wherein the RNP is immobilized to the substrate surface via the linker molecule, and
a guide ribonucleic acid (gRNA) comprising a first sequence bound to the RNP and a second sequence capable of binding to the target nucleic acid,
wherein conductivity of the substrate surface is modulated upon binding of target nucleic acid to the gRNA to thereby enable sensing of the target nucleic acid while the RNP-gRNA probe remains attached to the substrate surface.

10. A biosensor for assaying a target nucleic acid, the biosensor comprising:
a substrate comprising a substrate surface and at least two electrodes for passing current through the substrate, wherein the substrate surface comprises graphene;
a pyrenebutanoic acid (PBA) linker molecule comprising a pyrene ring moiety and a carboxylate moiety, wherein the linker molecule is conjugated to the substrate surface via interaction between the pyrene ring moiety and the substrate surface; and
an RNP-gRNA probe immobilized to the substrate surface via the linker molecule, the RNP-gRNA probe including
a ribonucleoprotein (RNP) comprising Cas9 protein coupled to a second moiety of the linker molecule via a carbodiimide bond, wherein the carbodiimide bond joins the linker molecule at the Recombination UV C (RuvC) domain of the Cas9 protein, and
a guide ribonucleic acid (gRNA) comprising a first sequence bound to the RNP and a second sequence capable of binding to the target nucleic acid,
wherein conductivity of the substrate surface is modulated upon binding of target nucleic acid to the gRNA to thereby enable sensing of the target nucleic acid while the RNP-gRNA probe remains attached to the substrate surface.

11. The biosensor of claim 9, wherein the substrate comprises a transistor comprising the at least two electrodes and the at least two electrodes comprise a source electrode, a drain electrode, and a gate electrode.

12. The biosensor of claim 11, wherein the transistor is a field-effect transistor (FET).

13. The biosensor of claim 9, further comprising an electronic controller capable of measuring a change in current on the substrate surface.

14. The biosensor of claim 10, wherein the substrate comprises a transistor comprising the at least two electrodes and the at least two electrodes comprise a source electrode, a drain electrode, and a gate electrode.

15. The biosensor of claim 14, wherein the transistor is a field-effect transistor (FET).

16. The biosensor of claim 10, further comprising an electronic controller capable of measuring a change in current on the substrate surface.

* * * * *

SEQUENCE LISTING

```
<160> NUMBER OF SEQ ID NOS: 5

<210> SEQ ID NO 1
<211> LENGTH: 23
<212> TYPE: DNA
<213> ORGANISM: Mus musculus

<400> SEQUENCE: 1
acagtcagcg gcaccctcat agg                                          23

<210> SEQ ID NO 2
<211> LENGTH: 18
<212> TYPE: DNA
<213> ORGANISM: Bacteriophage T7

<400> SEQUENCE: 2
taatacgact cactatag                                                18

<210> SEQ ID NO 3
<211> LENGTH: 44
<212> TYPE: DNA
<213> ORGANISM: Artificial Sequence
<220> FEATURE:
<223> OTHER INFORMATION: Guide RNA

<400> SEQUENCE: 3
gtttaagagc tatgctggaa acagcatagc aagtttaaat aagg                   44

<210> SEQ ID NO 4
<211> LENGTH: 60
<212> TYPE: DNA
<213> ORGANISM: Artificial Sequence
<220> FEATURE:
<223> OTHER INFORMATION: L2 terminal sgRNA

<400> SEQUENCE: 4
ggatcctaat acgactcact ataggctgaa gcactgcacg ccgtgtttta gagctagaaa  60

<210> SEQ ID NO 5
<211> LENGTH: 22
<212> TYPE: DNA
<213> ORGANISM: Aequorea victoria

<400> SEQUENCE: 5
gctgaagcac tgcacgccat gg                                           22
```